US006849634B2

(12) United States Patent
Beaudoin et al.

(10) Patent No.: US 6,849,634 B2
(45) Date of Patent: Feb. 1, 2005

(54) POTASSIUM CHANNEL INHIBITORS

(75) Inventors: Serge Beaudoin, Morrisvile, NC (US); Aimee D. Reed, Willoughby, OH (US); Michael F. Gross, Durham, NC (US)

(73) Assignee: ICAgen, Durham, NC (US)

( * ) Notice: Subject to any disclaimer, the term of this patent is extended or adjusted under 35 U.S.C. 154(b) by 33 days.

(21) Appl. No.: 10/004,867

(22) Filed: Dec. 7, 2001

(65) Prior Publication Data

US 2002/0161011 A1 Oct. 31, 2002

Related U.S. Application Data

(60) Provisional application No. 60/256,926, filed on Dec. 21, 2000.

(51) Int. Cl.$^7$ .......................... A61K 31/18; C07C 311/07

(52) U.S. Cl. ................... 514/256; 514/249; 514/258.1; 514/275; 514/278; 514/299; 514/388; 514/398; 514/399; 514/471; 514/472; 514/601; 514/602; 514/605; 544/230; 544/235; 544/253; 544/316; 544/332; 544/335; 544/349; 546/18; 546/112; 546/304; 546/314; 548/333.1; 548/335.5; 549/480; 549/492; 564/80; 564/92

(58) Field of Search .............................. 514/258.1, 249, 514/278, 299, 352, 357, 601, 602, 605, 230, 275, 471, 472; 544/235, 230, 253, 349, 316, 332, 335; 546/18, 112, 304, 314; 564/80, 92; 548/333.1, 335.5; 549/480, 492

(56) References Cited

U.S. PATENT DOCUMENTS

| | | | |
|---|---|---|---|
| 2,298,443 A | 10/1942 | Weissberger | 35/6 |
| 4,422,871 A | 12/1983 | Schirmer et al. | 71/120 |
| 4,975,453 A | 12/1990 | Becker et al. | 514/456 |
| 5,006,512 A | 4/1991 | Ohnishi | 514/21 |
| 5,215,985 A | 6/1993 | Murphy et al. | 514/212 |
| 5,234,947 A | 8/1993 | Cherksey | 514/449 |
| 5,242,947 A | 9/1993 | Cherksey et al. | 514/628 |
| 5,310,932 A | 5/1994 | Atwal et al. | 548/454 |
| 5,328,830 A | 7/1994 | Janis et al. | 435/21 |
| 5,356,775 A | 10/1994 | Hebert et al. | 435/6 |
| 5,401,758 A | 3/1995 | Atwal et al. | 514/353 |
| 5,401,848 A | 3/1995 | Atwal | 546/153 |
| 5,451,580 A | 9/1995 | Murphy et al. | 514/212 |
| 5,453,421 A | 9/1995 | Atwal et al. | 514/100 |
| 5,486,515 A | 1/1996 | Brown et al. | 514/229.8 |
| 6,015,822 A | 1/2000 | Brendel et al. | 514/357 |
| 6,083,986 A | 7/2000 | Castle et al. | 514/586 |
| 6,333,337 B1 | 12/2001 | Gross et al. | 514/307 |

FOREIGN PATENT DOCUMENTS

| | | |
|---|---|---|
| EP | 0 286 278 | 10/1988 |
| EP | 0 317 321 | 5/1989 |
| EP | 0 321 175 | 8/1989 |
| EP | 0 472 053 | 2/1992 |
| EP | 0 488 616 | 6/1992 |
| EP | 0 587 180 | 3/1994 |
| EP | 0 608 858 | 8/1994 |
| EP | 0915087 | 5/1999 |
| WO | 95/18617 | 7/1995 |
| WO | 95/26342 | 10/1995 |
| WO | WO 96/21640 A | 7/1996 |
| WO | WO 96/36596 | 11/1996 |
| WO | 97/25983 | 7/1997 |
| WO | 97/26300 | 7/1997 |
| WO | WO 98/04521 A | 2/1998 |
| WO | 9937607 | 7/1999 |
| WO | WO 00/12077 | 9/2000 |
| WO | WO 01/46155 A1 | 6/2001 |

OTHER PUBLICATIONS

Still, et al., "Rapid Chromatographic Technique for Preparative Separation with Moderate Resolution," J. Org. Chem., vol. 43, No. 14, 1978, 2923–2925.

Castle, et al., "Characterization of 4–Aminopyridne Block of the Transient Outward $K^+$ Current in Adult Rat Ventricular Myocytes," The Journal of Pharmacology and Experimental, vol. 264, No. 3, 1450–1459 (1993).

Deal, et al., "Molecular Physiology of Cardiac Potassium Channels," Physiological Reviews, vol. 76, No. 1, Jan. 1996, 49–67.

Wang, et al., "Sustained Depolarization–Induced Outward Current in Human Atrial Myocytes, Evidence for a Novel Delayed Rectified $K^+$ Current Similar to Kv1.5 Cloned Channel Current," Circulation Research, vol. 73, No. 6, Dec. 1993, 1061–1076.

Hamill, "Improved Patch–Clamp Techniques for High–Resolution Current Recording from Cells and Cell–Free Membrane Patches," Pflüger, Archiv, (1981) 391:85–100.

Fedida, et al., "Identity of a Novel Delayed Rectifier Current From Human Heart with a Cloned $K^+$ Channel Current," Circulation Research, vol. 73, No. 1, Jul. 1993, 210–216.

Chandy, et al., "Voltage–Gated Potassium Channels Are Required For Human T. Lymphocyte Activiation," J. Exp. Med., vol. 160, Aug. 1984, 369–385.

Sanguinetti, "Modulation of Potassium Channels by Anti-arrhythmic and Antihypertensive Drugs," Hypertension, vol. 19, No. E, Mar. 1992, 228–236.

Lynch, et al., "Therapeutic Potential of Modulating Potassium Currents in the Diseased Myocardium," The FASEB Journal, vol. 6, Aug. 1992, 2952–2960.

Colatsky, et al., "Channel Specificity in Antiarrhythmic Drug Action," Circulation, vol. 82, No. 6, Dec. 1990–2235–2242.

Halliwell, "$K^+$ Channels in the Central Nervous System," 348–381 (1988).

(List continued on next page.)

Primary Examiner—Richard L. Raymond
(74) Attorney, Agent, or Firm—Banner & Witcoff, Ltd.

(57) ABSTRACT

Compounds useful as potassium channel inhibitors and especially useful for the treatment of cardiac arrhythmias and cell proliferative disorders are described.

21 Claims, No Drawings

OTHER PUBLICATIONS

Amos, et. al. "*Differences Between Outward Currents of Human Atrial and Subepicardial Ventricular Myocytes,*" Journal of Physiology, (1986), 491.1, 31–50.

Wang, et al., "*Effects of Flecanide, Quinidine, and 4–Aminopyridine on Transient Outward and Ultrarapid Delayed Rectifier Currents in Human Atrial Myocytes,*" The Journal of Pharmacology and Experimental Therapeutics, vol. 272, No. 1, 184–196 (1995).

Lin, et al., "*Voltage–Gated Potassium Channel Regulate Calcium–dependent Pathways Involved in Human T Lymphocyte Activation,*" J. Exp. Med., vol. 177, 637–645 (1993).

Kaczorowki, et al., "*Lymphocyte Ion Channels as a Target for Immunosuppression,*" Perspective in Drug Discovery and Design 2 (1994) 233–248.

Leonard, et al., "*Selective Blockers of Voltage–Gated $K^+$ Channels Depolarize Human T Lymphocytes: Mechanism of the Antiproliferative Effect of Charybdotoxin*", vol. 89, 10094–10098, Nov. 1992.

International Search Report dated Jul. 7, 2002.

Gisbert Schneider, et al. "*Virtual Screening For Bioactive Molecules by Evolutionary De Novo Desing*", Angewandte Chemie, International Edition (200), 39(22), 4130–4133.

POTASSIUM CHANNEL INHIBITORS

This application claims the benefit under 35 U.S.C. § 119(e)(1) of prior filed provisional application 60/256,926, filed Dec. 21, 2000.

BACKGROUND OF THE INVENTION

1. Field of the Invention

The present invention is broadly directed to a class of compounds useful as potassium channel inhibitors.

2. Description of Related Art

The importance of potassium channels was first recognized almost fifty years ago when Hodgkin and Huxley discovered that potassium ions contributed to the current that excited the squid giant axon. Research in the area, however, was hampered by the lack of selective, high affinity ligands for potassium channels. But the advent of recombinant DNA techniques and single cell and whole cell voltage clamp techniques has changed the slow pace of the field. Indeed, potassium channels which exhibit functional, pharmacological and tissue distribution characteristics have been cloned. These cloned potassium channels are useful targets in assays for identifying candidate compounds for the treatment of various disease states. Potassium channels have turned out to be the most diverse family of ion channels discovered to date. They modulate a number of cellular events such as muscle contraction, neuro-endocrine secretion, frequency and duration of action potentials, electrolyte homeostasis, and resting membrane potential.

Potassium channels are expressed in eukaryotic and prokaryotic cells, and are elements in the control of electrical and nonelectrical cellular functions. Potassium channels have been classified according to their biophysical and pharmacological characteristics. Subclasses of these channels have been named based on amino acid sequence and functional properties. Salient among these are the voltage dependent potassium channels, for example voltage gated potassium channels (e.g., Kv1, Kv2, Kv3, Kv4). Subtypes within these subclasses have been characterized as to their putative function, pharmacology and distribution in cells and tissues (Chandy and Gutman, "Voltage-gated potassium channel genes" in Handbook of Receptors and Channels-Ligand and Voltage-gated Ion Channels, ed. R. A. North, 1995; Doupnik et al., *Curr. Opin. Neurobiol.* 5:268, 1995). For example, the Kv1 class of potassium channels is further subdivided depending on the molecular sequence of the channel, for example Kv1.1, Kv1.3, Kv1.5. Functional voltage-gated $K^+$ channels can exist as multimeric structures formed by the association of either identical or dissimilar subunits. This phenomenon is thought to account for the wide diversity of $K^+$ channels. However, subunit compositions of native $K^+$ channels and the physiologic role that particular channels play are, in most cases, still unclear.

Membrane depolarization by Kv1.3 inhibition has been shown to be an effective method to prevent T-cell proliferation and therefore has applications in many autoimmune conditions. Inhibition of $K^+$ channels in the plasma membrane of human T-lymphocytes has been postulated to play a role in eliciting immunosuppressive responses by regulating intracellular $Ca^{++}$ homeostasis, which has been found to be important in T-cell activation.

The Kv1.3 voltage-gated potassium channel is found in neurons, blood cells, osteoclasts and T-lymphocytes. The Chandy and Cahalan laboratories proposed a hypothesis that blocking the Kv1.3 channel would elicit an immunosuppressant response. (Chandy et al., *J. Exp. Med.* 160, 369, 1984; Decoursey et al., Nature, 307, 465, 1984). However, the $K^+$ channel blockers employed in their studies were nonselective. Until research with the peptide margatoxin, a peptide found in scorpion venom, no specific inhibitor of the Kv1.3 channel existed to test this hypothesis. Although a laboratory (Price et al, *Proc. Natl. Acad. Sci. USA*, 86, 10171, 1989) showed that charybdotoxin would block Kv1.3 in human T cells, charybdotoxin was subsequently shown to inhibit four different $K^+$ channels (Kv1.3 and three distinct small conductance $Ca^{++}$ activated $K^+$ channels) in human T-lymphocytes, limiting the use of this toxin as a probe for the physiological role of Kv1.3 (Leonard et al, *Proc. Natl. Acad. Sci. USA*, 89, 10094, 1992). Margatoxin, on the other hand, blocks only Kv1.3 in T-cells, and has immunosuppressant activity in both in vitro and in vivo models. (Lin et al., *J. Exp. Med.*, 177, 637, 1993). The therapeutic utility of this compound, however, is limited by its potent toxicity. Recently, a class of compounds has been reported that may be an attractive alternative to the above-mentioned drugs, see for example U.S. Pat. Nos. 5,670,504; 5,631,282; 5,696,156; 5,679,705; and 5,696,156. While addressing some of the activity/toxicity problems of previous drugs, these compounds tend to be of large molecular weight and are generally produced by synthetic manipulation of a natural product, isolation of which is cumbersome and labor intensive.

Immunoregulatory abnormalities have been shown to exist in a wide variety of autoimmune and chronic inflammatory diseases, including systemic lupuserythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of auto-antibodies and self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplants foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort. Therefore, a selective immunosuppressant without these side effects still remains to be developed. Potassium channel inhibitors promise to be the solution to this problem.

Atrial fibrillation (AF) is the most common sustained cardiac arrhythmia in clinical practice and is likely to increase in prevalence with the aging of the population. Currently, AF affects more than 1 million Americans annually, represents over 5% of all admissions for cardiovascular diseases and causes more than 80,000 strokes each year in the United States. While AF is rarely a lethal arrhythmia, it is responsible for substantial morbidity and can lead to complications such as the development of congestive heart failure or thromboembolism. Currently available Class I and Class III antiarrhythmic drugs reduce the rate of recurrence of AF, but are of limited use because of a variety of potentially adverse side effects including ventricular proarrhythmia. Because current therapy is inadequate and fraught with side effects, there is a clear need to develop new therapeutic approaches.

Antiarrhythmic agents of Class III are drugs that cause a selective prolongation of the duration of the action potential without significant cardiac depression. Available drugs in this class are limited in number. Examples such as sotalol and amiodarone have been shown to possess interesting Class III properties (Singh B. N., Vaughan Williams E. M. "A Third Class Of Anti-Arrhythmic Action: Effects On Atrial And Ventricular Intracellular Potentials And Other Pharmacological Actions On Cardiac Muscle, of MJ 1999 and AH 3747" Br. *J Pharmacol* 1970; 39:675–689. and Singh B. N., Vaughan Williams E. M, "The Effect Of Amiodarone, A New Anti-Anginal Drug, On Cardiac Muscle", Br *J Pharmacol* 1970; 39:657–667.), but these are not selective Class III agents. Sotalol also possesses Class II effects which may cause cardiac depression and is contraindicated in certain susceptible patients. Amiodarone, also is not a selective Class III antiarrhythmic agent because it possesses multiple electrophysiological actions and is severely limited by side effects (Nademanee, K. "The Amiodarone Odessey". *J Am. Coll. Cardiol.* 1992; 20:1063–065.) Drugs of this class are expected to be effective in preventing ventricular fibrillation. Selective class III agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration. Theoretically, prolongation of the cardiac action potential can be achieved by enhancing inward currents (i.e. $Na^+$ or $Ca^{++}$ currents; hereinafter $I_{Na}$ and $I_{Ca}$, respectively) or by reducing outward repolarizing potassium ($K^+$) currents. The delayed rectifier ($I_K$) $K^+$ current is the main outward current involved in the overall repolarization process during the action potential plateau, whereas the transient outward ($I_{to}$) and inward rectifier ($I_{K1}$) $K^+$ currents are responsible for the rapid initial and terminal phases of repolarization, respectively. Cellular electrophysiologic studies have demonstrated that $I_K$ consists of two pharmacologically and kinetically distinct $K^+$ current subtypes, $I_{Kr}$ (rapidly activating and deactivating) and $I_{Ks}$ (slowly activating and deactivating) (Sanguinetti and Jurkiewicz, Two Components Of Cardiac Delayed Rectifier $K^+$ Current: Differential Sensitivity To Block By Class IH Antiarrhythmic Agents, *J Gen Physiol* 1990, 96:195–215). Class III antiarrhythmic agents currently in development, including d-sotalol, dofetilide (UK-68,798), almokalant (H234/09), E-4031 and methanesulfonamide-N-[l'-6-cyano-1,2,3,4-tetrahydro-2-naphthalenyl)-3,4-dihydro4-hydroxyspiro[2H-1-benzopyran-2,4'-piperidin]-6yl] monochloride, predominantly, if not exclusively, block $I_{Kr}$. Although, amiodarone is a blocker of $I_{Ks}$ (Balser J. R. Bennett, P. B., Hondeghern, L. M. and Roden, D. M. "Suppression Of Time-Dependent Outward Current In Guinea Pig Ventricular Myocytes: Actions Of Quinidine And Amiodarone. *Circ. Res.* 1991, 69:519–529), it also blocks $I_{Na}$, and $I_{Ca}$, effects thyroid function, is a nonspecific adrenergic blocker, and acts as an inhibitor of the enzyme phospholipase (Nademanee, K. "The Amiodarone Odessey". *J. Am. Coll. Cardiol.* 1992; 20:1063–1065). Therefore, its method of treating arrhythmia is uncertain. Most Class III agents that are known to be in development predominantly block $I_{Kr}$.

Reentrant excitation (reentry) has been shown to be a prominent mechanism underlying supraventricular arrhythmias in man. Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging action potential duration (APD), prevents and/or terminates reentrant arrhythmias. Most selective Class III antiarrhythmic agents currently in development, such as d-sotalol and dofetilide predominantly, if not exclusively, block $I_{Kr}$, the rapidly activating component of $I_K$ found both in atrium and ventricle in man.

Since these $I_{Kr}$ blockers increase APD and refractoriness both in atria and ventricle without affecting conduction per se, theoretically they represent potential useful agents for the treatment of arrhythmias like AF. These agents have a liability in that they have an enhanced risk of proarrhythmia at slow heart rates. For example, torsades de points has been observed when these compounds are utilized (Roden, D. M. "Current Status of Class III Antiarrhythmic Drug Therapy", *Am J. Cardiol*, 1993; 72:44B–49B). This exaggerated effect at slow heart rates has been termed "reverse frequency-dependence", and is in contrast to frequency-independent or frequency-dependent actions (Hondeghern, L. M. "Development of Class III Antiarrhythmic Agents" *J. Cadiovasc. Cardiol.* 20 (Suppl. 2):S17–S22).

The slowly activating component of the delayed rectifier ($I_{Ks}$) potentially overcomes some of the limitations of $I_{Kr}$ blockers associated with ventricular arrhythmias. Because of its slow activation kinetics however, the role of $I_{Ks}$ in atrial repolarization maybe limited due to the relatively short APD of the atrium. Consequently, although $I_{Ks}$ blockers may provide distinct advantage in the case of ventricular arrhythmias, their ability to affect SVT is considered to be minimal.

The ultra-rapidly activating delayed rectifier $K^+$ current ($I_{kur}$) is believed to represent the native counterpart to a cloned potassium channel designated Kv1.5 and, while present in human atrium, it appears to be absent in human ventricle. Furthermore, because of its rapidity of activation and limited slow inactivation, $I_{kur}$ is believed to contribute significantly to repolarization in human atrium. Consequently, a specific blocker of $I_{kur}$, that is a compound which blocks Kv1.5, would overcome the shortcoming of other compounds by prolonging refractoriness by retarding repolarization in the human atrium without causing the delays in ventricular repolarization that underlie arrhythmogenic after depolarizations and acquired long QT syndrome observed during treatment with current Class III drugs.

In intact human atrial myocytes an ultra-rapidly activating delayed rectifier $K^+$ current $I_{kur}$ which is also known as the sustained outward current, $I_{sus}$ or $I_{so}$, has been identified and this current has properties and kinetics identical to those expressed by the human K⁺ channel clone (hKv1.5, HK2) when isolated from human heart and stably expressed in human (HEK-293) cell lines. (Wang, Fermini and Natel, 1993, Circ Res 73:1061–1076; Fedida et al., 1993, Circ Res 73:210–216; Snyders, Tamkun and Bennet, 1993, J Gen Physiol 101:513–543) and originally cloned from rat brain (Swanson et al., 10, Neuron 4:929–939). Although various antiarrythmic agents are now available on the market, those having both satisfactory efficacy and a high margin of safety have not been obtained. For example, antiarrythmic agents of Class I according to the classification scheme of Vaughan-Williams ("Classification Of Antiarrhythmic Drugs" In: Cardiac Arrhythmias, edited by: E. Sandoe, E. Flensted-Jensen, K. Olesen; Sweden, Astra, Sodertalje, pp449–472, 1981) which cause a selective inhibition of the maximum velocity of the upstroke of the action potential (max) are inadequate for preventing ventricular fibrillation. In addition, they have problems regarding safety, namely, they cause a depression of myocardial contractility and have a tendency to induce arrhythmias due to an inhibition of impulse conduction. Beta-adrenoceptor blockers and calcium antagonists which belong to Class II and IV, respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

The present invention is related to compounds which are useful as inhibitors of potassium channel function. The compounds of the invention are especially active as inhibitors of voltage-gated potassium channels. The potassium channel inhibitors of the invention may therefore be utilized for the treatment of diseases in which prolongation of cellular action potentials would be beneficial, which include, but are not limited to, cardiac arrhythmias. In addition, compounds of the invention may be utilized for treating disorders in which induction of cell membrane depolarization would be beneficial, which include, but are not limited to, cell proliferative disorders.

WO 98/04521 (see also U.S. Pat. No. 6,083,986) describes a class of indane potassium channel inhibitors said to be useful for treating cardiac arrhythmias and cell proliferative disorders.

It is an object of the present invention to provide compounds which are useful for the treatment of diseases in mammals, including humans, and especially for the management of diseases which can be treated by inhibiting cell membrane potassium channels, such as the potassium channels responsible for cardiac $I_{Kur}$ potassium current, or the potassium channels responsible for T-lymphocyte $I_{Kn}$ potassium current, and potassium channels containing one of Kv1.5 or Kv1.3 α-subunit gene products.

Another object of the invention is to provide a method of treating diseases in mammals, including humans, which respond to the inhibition of potassium channel function, which method comprises administering to a mammal in need thereof a compound of the invention.

DETAILED DESCRIPTION OF THE INVENTION

This invention describes compounds and their utility as inhibitors of voltage-dependent potassium channel function, particularly potassium channels (i.e., $I_{Kur}$, Kv1.5) that could serve as targets for the treatment of cardiac arrhythmias especially those occurring in the atria (e.g., atrial flutter and atrial fibrillation) (Wang et al., Circ. Res. 73:1061, 1993; Fedida et al., Circ. Res. 73:210, 1993; Wang et al., J. Pharmacol. Exp. Ther. 272:184, 1995), as well as the potassium channels (i.e., $I_{Kn}$, Kv1.3) that could serve as targets for the treatment of immunologic diseases (Kaczorowski and Koo, Perspectives in Drug Discovery and Design 2:233, 1994). Consequently, the present invention also provides a method for treating diseases which respond to the inhibition of potassium channel function, such as cardiac arrhythmias and various immunologic diseases, using the compounds of the invention.

The invention is particularly based on our discovery that the compounds of the following formula (I) are inhibitors of potassium channel function. In particular, these compounds have demonstrated activity against the human potassium channels/currents $I_{Kur}$, $I_{Kn}$, Kv1.5, and Kv1.3. As a result, these compounds are useful in the treatment of cardiac arrhythmias and cell proliferative disorders.

Thus, in a first aspect, the present invention concerns compounds having potassium channel inhibitory activity of the formula (I), or a pharmaceutically acceptable salt or prodrug thereof

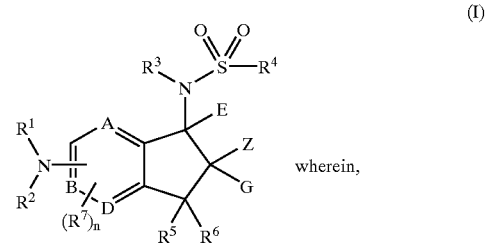

wherein,

A, B, and D are selected from a substituted carbon atom, a nitrogen atom or N→O, wherein at least one of A, B, and D is a substituted carbon atom and at most only one of A, B and D is N→O;

E is hydrogen, or alkyl; G is hydrogen, or alkyl; or E and G taken together form a bond (site of unsaturation);

$R^1$ is selected from hydrogen, alkyl, carbocycloalkyl, aryl, (aryl)alkyl, heterocyclo, (heterocyclo)alkyl, heteroaryl and (heteroaryl)alkyl;

$R^2$ is selected from alkyl, carbocycloalkyl, aryl, (aryl)alkyl, heterocyclo, (heterocyclo)alkyl, heteroaryl and (heteroaryl)alkyl;

$R^3$ is selected from hydrogen (H), alkyl, carbocycloalkyl, aryl, (aryl)alkyl, heterocyclo, (heterocyclo)alkyl, heteroaryl, (heteroaryl)alkyl, aminoalkyl; substituted aminoalkyl, carboxyalkyl, alkoxyalkanoyl, aminoalkanoyl, substituted aminoalkanoyl, alkanoylamidoalkyl, alkanoyl(substituted amido)alkyl, aroylamidoalkyl, aroyl(substituted amido)alkyl, heterocyclocarbonylamidoalkyl, heterocyclocarbonyl (substituted amido)alkyl, heteroaroylamidoalkyl, and heteroaroyl(substituted amido)alkyl;

$R^4$ is selected from alkyl, carbocycloalkyl, aryl, (aryl)alkyl, heteroaryl and heterocyclo;

$R^5$ and $R^6$ are each independently selected from hydrogen, fluoro and alkyl, or $R^5$ and $R^6$ taken together, along with the carbon atom to which they are both attached, form a 3-membered to 7-membered carbocyclic, or heterocyclic ring;

$R^7$ is independently selected from hydrogen, alkyl, hydroxy, alkoxy, amino, substituted amino, nitro, cyano, halo, carboxy, alkoxycarbonyl, aminocarbonyl, substituted aminocarbonyl and n is 1, 2 or 3;

Z is selected from hydrogen, alkyl, hydroxy, SH, alkoxy, aryloxy, alkylthio, amino, substituted amino, alkoxycarbonyl, alkanoylamido, aroylamido, heterocyclocarbonylamido, heteroaroylamido, alkanoyl(alkylsubstituted) amido, aroyl(alkylsubstituted)amido, heteroaroyl(alkylsubstituted) amido, and heterocyclocarbonyl(alkyl substituted) amido.

One preferred subclass of heteroaryls for $R^2$ is:

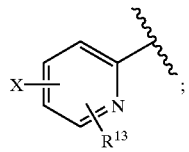

wherein

X is selected from substituted amino, —N($R^8$)CO$R^9$, —N($R^8$)SO$_2R^{10}$, and —CO—NR$^{11}$R$^{12}$;

$R^8$ is selected from hydrogen (H), alkyl, aryl and heteroaryl;

$R^9$ is selected from alkyl, carbocycloalkyl, alkenyl, alkynyl, aryl, alkoxy, aryloxy, heterocyclo, heteroaryl, (aryl)alkyl, (heteroaryl)alkyl, amino and substituted amino;

$R^{10}$ is selected from alkyl, aryl, heterocyclo and heteroaryl;

$R^{11}$ is selected from hydrogen(H), alkyl, carbocycloalkyl, aryl, heterocyclo, heteroaryl, (aryl)alkyl, (heterocyclo)alkyl, (heteroaryl)alkyl, aminoalkyl and substituted aminoalkyl;

$R^{12}$ is selected from hydrogen (H), alkyl, carbocycloalkyl, aryl, heterocyclo, heteroaryl, (aryl)alkyl, (heterocyclo)alkyl, (heteroaryl)alkyl, aminoalkyl and substituted aminoalkyl, or $R^{11}$ and $R^{12}$ taken together, along with the nitrogen atom to which they are both attached, form a 4-membered to 8-membered heterocyclic ring;

$R^{13}$ is selected from hydrogen (H), alkyl, aryl, hydroxy, alkoxy, amino, substituted amino, nitro, cyano and halo;

In a preferred class of compounds of formula (I), A, B and D are substituted carbon atoms, E, G, $R^5$, $R^6$ and $R^7$ are each a hydrogen, n is 3, Z is the same as noted above in connection with formula (I), and preferably is selected from hydrogen, alkyl, hydroxyl, amino and substituted amino, and the remaining substituents are as defined above in connection with formula (I), as is represented in the following formula (II), (and again including the pharmaceutically acceptable salts or prodrugs thereof)

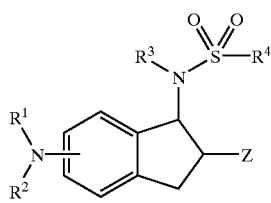

In a more preferred subset of compounds of formula (II) (and their pharmaceutically acceptable salts, or prodrugs), $R^1$ is selected from H, alkyl, carbocycloalkyl, (aryl)alkyl, heterocyclo, (heterocyclo)alkyl, heteroaryl and (heteroaryl)alkyl; $R^2$ is selected from alkyl, carbocycloalkyl, aryl, (aryl)alkyl, heterocyclo, (heterocyclo)alkyl, heteroaryl and (heteroaryl)alkyl; Z is selected from hydrogen, hydroxyl, amino and substituted amino and $R^3$ and $R^4$ are the same as defined above in connection with formula (I).

A more preferred subclass of heteroaryls for $R^2$ in this case is:

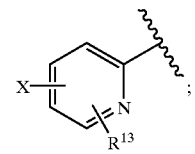

wherein X is selected from —N($R^8$)CO$R^9$ and —CO—NR$^{11}$R$^{12}$; $R^8$ is selected from H and alkyl; $R^9$ is selected from alkyl, carbocycloalkyl, alkenyl, alkynyl, aryl, alkoxy, aryloxy, heterocyclo, heteroaryl, (aryl)alkyl, (heteroaryl)alkyl, amino and substituted amino; $R^{11}$ is selected from hydrogen, alkyl, carbocycloalkyl, aryl, heterocyclo, heteroaryl, (aryl)alkyl, (heterocyclo)alkyl, (heteroaryl)alkyl, aminoalkyl and substituted aminoalkyl; $R^{12}$ is selected from hydrogen, alkyl, carbocycloalkyl, aryl, heterocyclo, heteroaryl, (aryl)alkyl, (heterocyclo)alkyl, (heteroaryl)alkyl, aminoalkyl and substituted aminoalkyl, or $R^{11}$ and $R^{12}$ taken together, along with the nitrogen atom to which they are both attached, form a 4-membered to 8-membered heterocyclic ring; and $R^{13}$ is selected from hydrogen, alkyl, hydroxy, alkoxy, amino, substituted amino, nitro, cyano and halo.

In another aspect, the present invention concerns indane compounds having potassium channel inhibition activity of the formula (III), or pharmaceutically acceptable salts or prodrugs thereof:

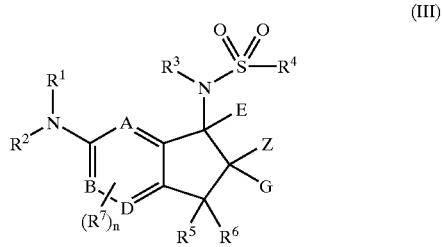

wherein all of the variables have the meaning ascribed to them in connection with formula (I).

Yet another preferred subclass of compounds (including their pharmaceutically acceptable salts or prodrugs) falling within the compounds of formula (I) is represent by the following formula (IV):

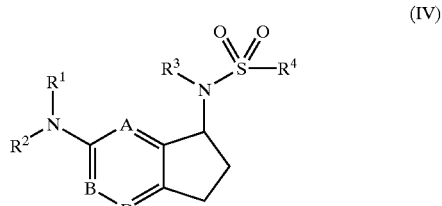

wherein all of the variables have the meaning ascribed to them in connection with formula (II).

In a preferred class of the compounds of formula (IV) (including pharmaceutically acceptable salts or prodrugs thereof), $R^1$ is selected from H, alkyl, carbocycloalkyl, (aryl)alkyl, heterocyclo, (heterocyclo)alkyl, heteroaryl, (heteroaryl)alkyl and substituted aminoalkyl; $R^2$ is selected from alkyl, carbocycloalkyl, aryl, (aryl)alkyl, heterocyclo, (heterocyclo)alkyl, heteroaryl, (heteroaryl)alkyl and

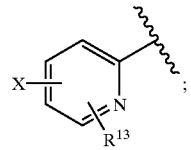

X is selected from —N($R^8$)CO$R^9$ and —CO—N$R^{11}R^{12}$; $R^8$ is selected from H and alkyl; $R^9$ is selected from alkyl, carbocycloalkyl, alkenyl, alkynyl, aryl, alkoxy, aryloxy, heterocyclo, heteroaryl, (aryl)alkyl, (heteroaryl)alkyl, amino and substituted amino; $R^{11}$ is selected from hydrogen, alkyl, carbocycloalkyl, aryl, heterocyclo, heteroaryl, (aryl)alkyl, (heterocyclo)alkyl, (heteroaryl)alkyl, aminoalkyl and substituted aminoalkyl; $R^{12}$ is selected from hydrogen, alkyl, carbocycloalkyl, aryl, heterocyclo, heteroaryl, (aryl)alkyl, (heterocyclo)alkyl, (heteroaryl)alkyl, aminoalkyl and substituted aminoalkyl, or $R^{11}$ and $R^{12}$ taken together, along with the nitrogen atom to which they are both attached, form a 4-membered to 8-membered heterocyclic ring; $R^{13}$ is selected from hydrogen, alkyl, hydroxy, alkoxy, amino, substituted amino, nitro, cyano and halo; Z is selected from hydrogen, hydroxyl, amino and substituted amino and $R^3$ and $R^4$ are the same as defined above in connection with formula (I).

Specific examples of molecules embraced under formulae (I) through (IV) are illustrated below in Table 1.

As used herein, when a particular radical generally understood to have a single point of attachment to a core structure, such as an alkyl group, is identified in connection with a structure that must have two points of attachment in the structural core (such as with the moiety (aryl)alkyl), it is understood that the named radical, e.g., alkyl, refers to the parent radical with a hydrogen or, in the case of an unsaturated moiety, a site of unsaturation removed to create the second point of attachment so as to provide the required structure.

The term "alkyl," as used alone or in combination herein, refers to an unsubstituted or optionally substituted, straight, or branched chain saturated hydrocarbon group containing from one to eight carbon atoms, preferably from one to five carbons, such as methyl, ethyl, n-propyl, n-butyl, pentyl, hexyl, heptyl, octyl, the various branch chain isomers thereof, such as isopropyl, isobutyl, sec-butyl, tert-butyl, isohexyl and the like. The alkyl group may be optionally substituted by one or more substituents, and generally no more than three, and most often just one substituent. Preferred optional substituents include halo, alkoxy, amino, mono- and di-substituted amino, aryl, carboxylic acid, heterocyclo, heteroaryl, carbocycloalkyl, hydroxy, trifluoromethoxy and the like. The term "lower alkyl" refers to such alkyl groups containing from one to five carbon atoms.

The term "alkoxy," as used alone or in combination herein, refers to an alkyl group, as defined above, covalently bonded to the parent molecule through an —O— linkage, such as methoxy, ethoxy, propoxy, isopropoxy, butoxy, t-butoxy and the like.

The term "alkoxyalkyl" refers specifically to an alkyl group substituted with an alkoxy group (R—O-alkyl-).

The term "aryloxy," as used alone or in combination herein, refers to an aryl group, as defined below, covalently bonded to the parent molecule through an —O— linkage. An example of an aryloxy is phenoxy.

The term "cycloalkoxy," as used alone or in combination herein, refers to a carbocycloalkyl group, preferably a cycloalkyl group, as both defined below, covalently bonded to the parent molecule through an —O— linkage.

The term "alkylthio," as used alone or in combination herein, refers to an alkyl group, as defined above, covalently bonded to the parent molecule through an —S— linkage.

The term "alkenyl," as used alone or in combination herein, refers to an alkyl group, as defined above, containing one or more carbon-to-carbon double bonds, preferably one or two double bonds. Examples of alkenyl include ethenylene, propenylene, 1,3-butadienyl, and 1,3,5-hexatrienyl.

The term "alkynyl," as used alone or in combination herein, refers to an alkyl group, as defined above, containing one or more carbon-to-carbon triple bonds, preferably one or two triple bonds.

The term "cycloalkyl," as used alone or in combination herein, refers to an unsubstituted or optionally substituted, saturated cyclic hydrocarbon group containing three to eight carbon atoms. The cycloalkyl group may optionally be substituted by one or more substituents, and generally no more than three, and most often just one substituent. Preferred optional substituents include alkyl, halo, amino, mono- and di-substituted amino, aryl, hydroxy, heterocyclo, heteroaryl and the like.

The term "haloalkyl" is a species of alkyl as defined herein, and particularly refers to an alkyl, preferably a lower alkyl, substituted with one or more halogen atoms, and preferably is a $C_1$ to $C_4$ alkyl substituted with one to three halogen atoms. Examples of a haloalkyl include trifluoromethyl and difluoromethyl.

The term "alkanoyl" as used alone or in combination herein refers to an acyl radical derived from an alkanecarboxylic acid (alkyl-C(O)—), particularly a lower alkanecarboxylic acid, and includes such examples as acetyl, propionyl, butyryl, valeryl, and 4-methylvaleryl.

The term "aroyl" means an acyl radical derived from an aromatic carboxylic acid, such as optionally substituted benzoic or naphthoic acids and specifically including benzoyl (($C_6H_5$)—C(O)—) and 1-naphthoyl.

The term "aminocarbonyl" means an amino-substituted carbonyl (carbamoyl or carboxamide) wherein the amino group is a primary amino (—$NH_2$). Substituted aminocarbonyl refers to secondary (mono-substituted amino) or tertiary amino (di-substituted amino) group, as defined below, preferably having as a substituent(s) a lower alkyl.

The term "aminoalkanoyl" means an amino-substituted alkanoyl wherein the amino group is a primary amino (-alkyl-C(O)—$NH_2$). The term "substituted aminoalkanoyl" refers to related secondary (mono-substituted amino) or tertiary amino (di-substituted amino) group, as defined below.

The term "carbocycloalkyl" when used alone or in combination refers to an unsubstituted or optionally substituted, stable, saturated or partially unsaturated monocyclic, bridged monocyclic, bicyclic, and spiro ring carbocycles of 3 to 15 carbon atoms such as cyclopropyl, cyclobutyl, cyclopentyl, cyclohexyl, cycloheptyl, bicyclohexyl, bicyclooctyl, bicyclononyl, spirononyl and spirodecyl. Cycloalkyls are thus one specific subset of carbocycloalkyls, and in the context of the present invention constitute a highly preferred subset. The term "optionally substituted" as it refers to "carbocycloalkyl" herein indicates that the carbocycloalkyl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Generally, there is no more than one optional substituent.

The term "heterocyclo" as used, alone or in combination, herein refers to an unsubstituted or optionally substituted, stable, saturated, or partially unsaturated, monocyclic, bridged monocyclic, bicyclic, and spiro ring system containing carbon atoms and other atoms selected from nitrogen, sulfur and/or oxygen. Preferably, a heterocyclo is a 5 or 6-membered monocyclic ring or an 8–11 membered bicyclic ring which consists of carbon atoms and contains one, two, or three heteroatoms selected from nitrogen, oxygen and/or sulfur. Heterocyclo includes benz-fused monocyclic carbocycloalkyl groups having at least one such heteroatom. The term "optionally substituted" as it refers to "heterocyclo" herein indicates that the heterocyclo group may be substituted at one or more substitutable ring positions by one or more groups independently selected from alkyl (preferably lower alkyl and including haloalkyl (preferably trifluoromethyl)), alkoxy (preferably lower alkoxy), nitro, monoalkylamino (preferably a lower alkylamino), dialkylamino (preferably a di[lower] alkylamino), cyano, halo, alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Generally, there is no more than two, and usually no more than one, optional substituent. Several non-limiting examples of such heterocyclo groups are illustrated below:

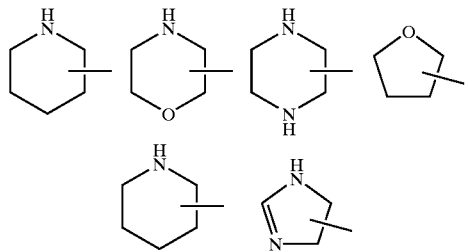

The heterocyclo group may be, and generally is attached to the parent structure through a carbon atom, or alternatively may be attached through any heteroatom of the heterocyclo that results in a stable structure.

The term "heteroaryl" as used alone or in combination, herein refers to an unsubstituted or optionally substituted, stable, aromatic monocyclic or bicyclic ring system containing carbon atoms and other atoms selected from nitrogen, sulfur and/or oxygen. Preferably, a heteroaryl is a 5 or 6-membered monocyclic ring (optionally benzofused) or an 8–11 membered bicyclic ring which consists of carbon atoms and contains one, two, or three heteroatoms selected from nitrogen, oxygen and/or sulfur. The term "optionally substituted" as it refers to "heteroaryl" herein indicates that the heteroaryl group may be substituted at one or more substitutable ring positions by one or more groups independently selected from alkyl (preferably lower alkyl and including haloalkyl (preferably trifluoromethyl)), alkoxy (preferably lower alkoxy), nitro, monoalkylamino (preferably a lower alkylamino), dialkylamino (preferably a di[lower]alkylamino, cyano, halo, alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Generally, there is no more than two, and usually no more than one, optional substituent. Several non-limiting examples of such heteroaryl groups are illustrated below:

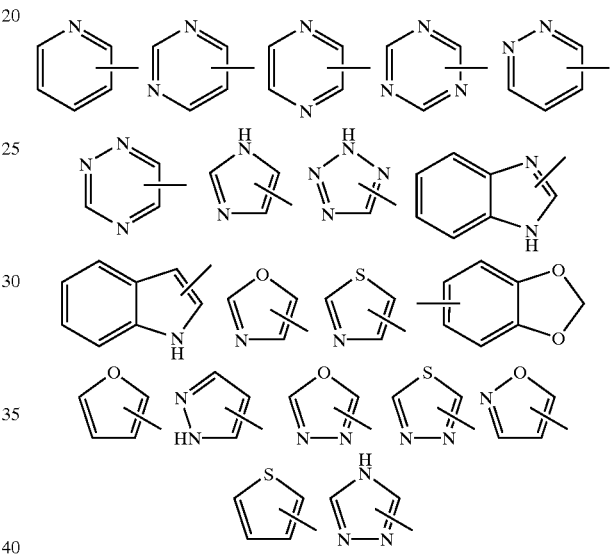

The heteroaryl group may be, and generally is attached to the parent structure through a carbon atom or alternatively maybe attached through any heteroatom of the heteroaryl that results in a stable structure. In the foregoing structures it also is contemplated that a nitrogen could be replaced with an N-oxide.

Both heterocyclo and heteroaryl also are intended to embrace benzo fused structures such as 1,2-methylenedioxybenzene and 1,4-benzodioxan.

The specific chemical nature of the optionally substituted heterocyclo and heteroaryl groups for the terminal moieties $R^1$ and $R^2$ in the prior identified potassium channel inhibitor compounds is not narrowly critical and, as noted above, a wide variety of substituent groups are contemplated. Preferably, the substituents for the heterocyclo and heteroaryl groups are selected such that the total number of carbon and hetero atoms comprising the substituted heterocyclos and heteroaryls is no more than about 20.

The terms "halo" and "halogen" as used herein to identify substituent moieties, represent fluorine, chlorine, bromine or iodine, preferably chlorine or fluorine.

The term "aryl," when used alone or in combination, refers to an unsubstituted or optionally substituted monocyclic or bicyclic aromatic hydrocarbon ring system having 6 to 12 ring carbon atoms. Preferred are optionally substituted phenyl, 1-naphthyl, or 2-naphthyl groups. The aryl group may optionally be substituted at one or more substitutable ring positions (generally at no more than three positions and most often at one or two positions) by one or more groups independently selected from alkyl (including haloalkyl (preferably trifluoromethyl and difluoromethyl)), alkenyl, alkynyl, alkoxy, aryloxy, nitro, hydroxy, amino, mono- and di-substituted amino, cyano, halo, alkanoyl, aminocarbonyl, carboxylic acid, carboxylic acid esters, carboxylic acid amide, an optionally substituted phenyl (optionally substituted by halo, lower alkyl and lower alkoxy groups), heterocyclo, or heteroaryl. Preferably, the aryl group is phenyl optionally substituted with up to four and more usually with one or two groups, preferably selected from lower alkyl, lower alkoxy, as well as cyano, trifluoromethyl and halo.

The terms "aralkyl" and "(aryl)alkyl," alone or in combination are a species of alkyl as defined herein, and particularly refers to an alkyl group as defined above in which one hydrogen atom is replaced by an aryl group as defined above, and includes benzyl, and 2-phenylethyl.

The terms "(heterocyclo)alkyl" and "(heteroaryl)alkyl" alone or in combination can be considered a species of alkyl as defined herein, and particularly refers to an to an alkyl group as defined above in which one hydrogen atom is replaced by a heterocyclo group as defined above, such as tetrahydrofurfuryl, or by a heteroaryl group as defined above, such as furfuryl.

The term "alkoxycarbonyl" alone or in combination means a radical of the formula —C(O)-alkoxy, in which alkoxy is as defined above.

The term "alkylcarbonyloxy" alone or in combination means a radical of the formula —O—C(O)-alkyl, in which alkyl is as defined above.

The term "alkoxyalkanoyl" alone or in combination means a radical of the formula -alkyl-C(O)—O-alkyl.

The term "carboxyalkyl" alone or in combination means a radical of the formula -alkyl-C(O)—OH.

As used in connection with formula (I) and elsewhere in this application, the term "substituted carbon atom" means a ring carbon substituted with one of the group $R^7$, or the radical —N($R^2$)($R^1$).

The term "substituted amino" embraces both "mono- and di-substituted amino." These terms, alone, or in combination, mean a radical of the formula —NR'R", where, in the case of mono-substitution, one of R' and R" is a hydrogen and the other is selected from alkyl, carbocycloalkyl, aryl, heterocyclo, (aryl)alkyl, (heterocyclo)alkyl, heteroaryl and (heteroaryl)alkyl; in the case of di-substitution, R' and R" are independently selected from alkyl, carbocycloalkyl, aryl, heterocyclo, and heteroaryl, or R' and R" together with the nitrogen atom to which they are both attached form a three to eight-membered heterocyclo or heteroaryl radical.

The term "aminoalkyl" means $H_2N$-alkyl-, while substituted aminoalkyl embraces both mono- and di-substitution and means R'R"N-alkyl- with, in the case of mono-substitution, one of R' and R" being a hydrogen and the other being selected from alkyl, carbocycloalkyl, aryl, heterocyclo, (aryl)alkyl, (heterocyclo)alkyl, heteroaryl and (heteroaryl)alkyl; and in the case of di-substitution, R' and R" being independently selected from alkyl, carbocycloalkyl, aryl, heterocyclo, and heteroaryl, or R' and R" together with the nitrogen atom to which they are both attached forming a three to eight-membered heterocyclo or heteroaryl radical as defined above for substituted amino.

The term "amido" refers to the group (—NH—) and the term "substituted amido" embraces a radical of the formula (—NR'—) where R' has the meaning above in connection with substituted amino.

The terms "alkanoylamido," "aroylamido," "heterocyclocarbonylamido" and "heteroaroylamido" mean groups of the formula R—C(O)—NH— where R is an alkyl, aryl, heteroaryl or heterocyclo. The terms "alkanoyl(substituted) amido," "aroyl(substituted)amido," "heterocyclocarbonyl (substituted)amido" and "heteroaroyl(substituted)amido" mean groups of the formula R—C(O)—NR'— where R is an alkyl, aryl, heteroaryl or heterocyclo and where R' has the meaning above in connection with substituted amino. For example, in an alkanoyl(alkylsubstituted) amido, both R and R' would be alkyls.

The terms "alkanoylamidoalkyl," "aroylamidoalkyl," "heterocyclocarbonylamidoalkyl" and "heteroaroylamidoalkyl" mean groups of the formula R—C(O)—NH-alkyl- where R is an alkyl, aryl, heteroaryl or heterocyclo.

The terms "heteroaroyl" and "heterocyclocarbonyl" when used alone or in combination means groups of the formula R—C(O)— where R is a heteroaryl or heterocyclo.

Unless otherwise defined, the term "optionally substituted" as used herein, refers to the substitution of a ring system at one or more positions with one or more groups selected from: $C_{1-5}$ alkyl, $C_{1-5}$ alkoxy, an optionally substituted phenyl, cyano, halo, trifluoromethyl, $C_{1-5}$ alkoxycarbonyl, $C_{1-5}$ alkyl carbonyloxy, mono- and bis-($C_{1-5}$ alkyl)-carboxamide, $C_{1-5}$ alkyl amido, nitro, and mono- and bis-($C_{1-5}$ alkyl)-amino.

Applicants recognize that there maybe some overlap in some of the definitions of the various radical groups. Specific groups are mentioned, however, such as (aryl)alkyl, and may be particularly identified in the claims, in order to emphasize their positive inclusion in the described subject matter, and not as only an optional substituent.

The foregoing definitions are illustrative of possible substituents for compounds falling within the scope of the present invention. As those skilled in the art of medicinal chemistry well understand, any combination of suitable substituents is selected in order to provide a stable compound structure. Thus, particular substituents and groups of substituents are chosen such that compound stability is obtained and preserved.

The term "treating" as used herein, describes the management and care of a patient afflicted with a condition, disease or disorder for which the administration of a compound of the present invention alters the action or activity of a potassium channel to prevent the onset of symptoms or complications associated with the condition, disease or disorder, to alleviate the symptoms or complications caused by the condition, disease or disorder, or to eliminate the condition, disease or disorder altogether.

Certain indane compounds of the previous formulae useful as potassium channel inhibitors in accordance with the present invention can be prepared in accordance with the following Scheme 1:

SCHEME 1

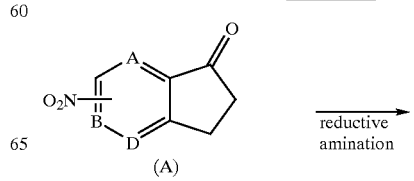

(A) reductive amination

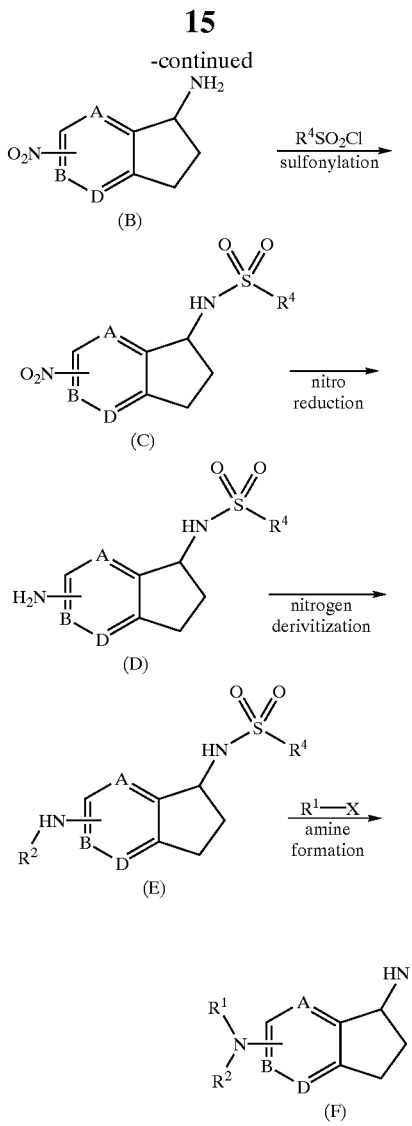

alkylation using an aldehyde and a drying agent such as sodium sulfate followed by treatment with a reducing agent such as sodium borohydride in an organic solvent such as methanol or ethanol.

The secondary amine (E) may thereafter be further derivatized in step (5) by reacting the secondary amine (E) with an agent such as an alkyl halide to form the amine compounds (F) of formula II.

The starting nitro indanone, compound (A), the amino compound (B), the sulfonamide (C), and the aniline (D) in General Scheme 1 may be prepared as described in N. Castle et al., WO 9804521 (see also U.S. Pat. No. 6,083,986 incorporated in its entirety herein by reference).

A synthetic approach to prepare compounds of the invention, such as those of formula II, where Z is hydroxyl and $R^3$ is hydrogen is provided by the following synthesis scheme (Steps 1–8). In step (1), reduction of a nitro indanone (using $NaBH_4$ for example) gives the corresponding alcohol;

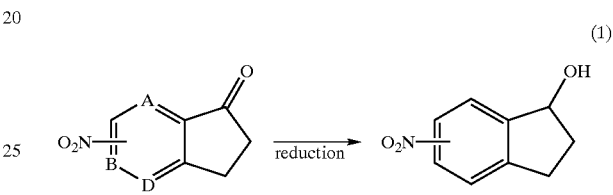

In the next step (2), the product of step (1) is subjected to an acid catalyzed dehydration (pTSA/Toluene) to give the corresponding indene.

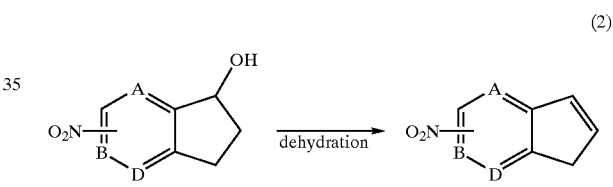

Then in step (3) the double bond of the indene product of step (2) is oxidized (e.g. using $M-CPBA/CH_2Cl_2$) to give the corresponding epoxide.

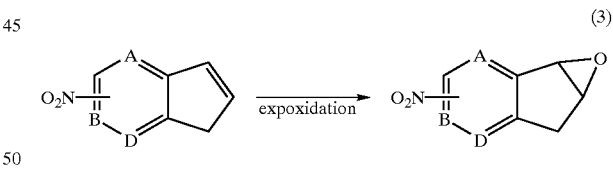

In step (4), the epoxide of step (3) is aminated (for instance using ammonium hydroxide) to give the corresponding amino alcohol.

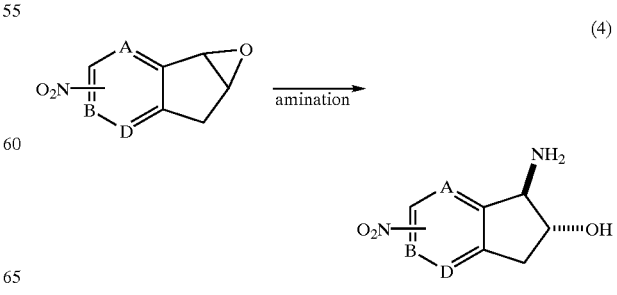

Compounds of the invention, such as those of formula II, where Z is hydrogen and $R^3$ is hydrogen may be prepared starting with a nitro indanone (A), which in step (1) is reductively aminated in the presence of ammonium acetate (employing a molar ratio of nitro indanone:ammonium acetate within the range from about 1:1 to about 1:30) and a reducing agent such as sodium cyanoborohydride in an inert organic solvent such as methanol to form the nitro-amino compound (B). The nitro-amino compound (B) then is reacted with a sulfonylating agent (employing a molar ratio of Step (1) product to sulfonylating agent within the range from about 1:1 to about 10:1) in the presence of a base such as triethylamine or pyridine and in an inert organic solvent such as tetrahydrofuran or dichloromethane to form the sulfonylated compound (C).

The sulfonylated compound (C) is then subjected to nitro-reduction by treatment with a suitable reducing agent such as sodium borohydride in the presence of nickel chloride in an organic solvent such as tetrahydrofuran and/or methanol to form the aniline (D). Aniline (D) is then derivatized by treatment with an alkylating agent such as an alkyl halide ($R^2X$ where X is Cl, Br, or I) in the presence of a base such as potassium carbonate in an inert solvent such as acetonitrile to form the secondary amine (E). Alternatively, aniline (D) can be derivatized by reductive The amino-alcohol of step (4) is sulfonylated, for example using a sulfonyl chloride, to attach an $R^4$—$SO_2$-moiety. The amino-alcohol is reacted in a suitable solvent with the sulfonyl chloride (or a sulfonyl anhydride) in the presence of an acid scavenger. Suitable solvents in which the reaction can be conducted include methylene chloride and tetrahydrofuran. Suitable acid scavengers include triethylamine and pyridine.

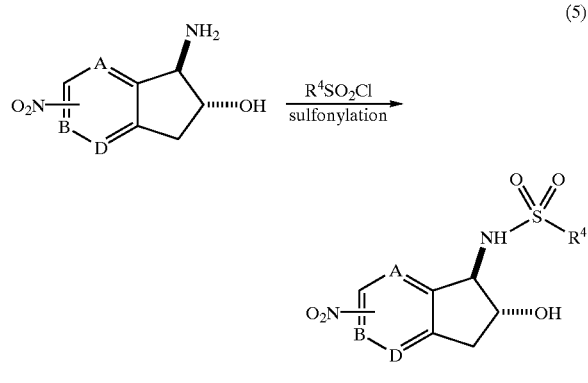

In step (6), the nitro moiety of the sulfonylated product of step (5) is reduced ($SnCl_2$) to give the corresponding aniline.

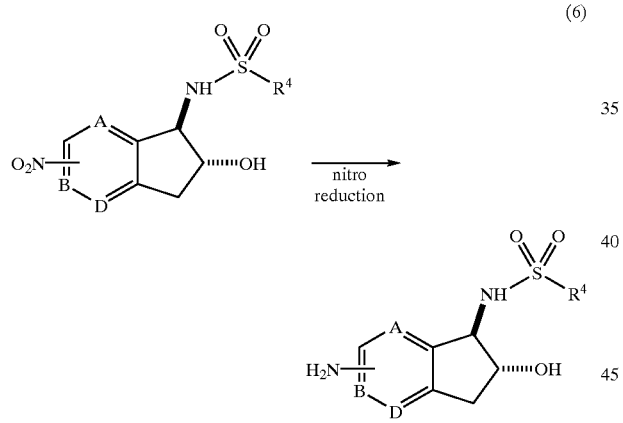

The aniline formed in step (6) can then be derivatized (step (7)) by treatment with an alkylating agent such as an alkyl halide ($R^2X$ where X is Cl, Br, or I) in the presence of a base such as potassium carbonate in an inert solvent such as acetonitrile to form a secondary amine. Alternatively, the aniline formed in step (6) can be derivatized by reductive alkylation using an aldehyde and a drying agent such as sodium sulfate followed by treatment with a reducing agent such as sodium borohydride in an organic solvent such as methanol or ethanol. The —OH moiety may be protected by a suitable protecting group at any suitable point in the synthesis, such as prior to any aniline derivatization step. One skilled in the art will recognize that there are a variety of hydroxy protecting groups as discussed in "Protective Groups in Organic Synthesis", T. W. Green and P. G. M. Wuts (1999).

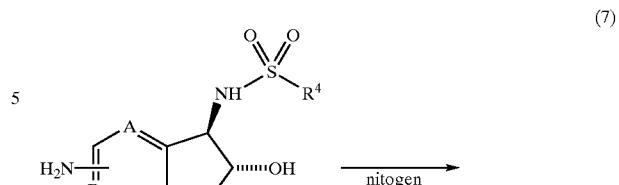

As in Scheme 1, the so-formed secondary amine thereafter undergoes further derivitization in step (8).

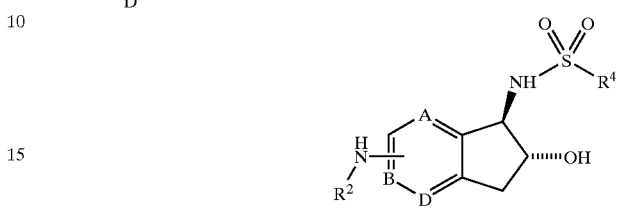

Certain preferred compounds of the present invention can be prepared in accordance with the procedures of Scheme 1, given the selection of appropriate starting materials, as follows (starting with the nitrogen derivitization step), where the variables have the meanings identified throughout this application.

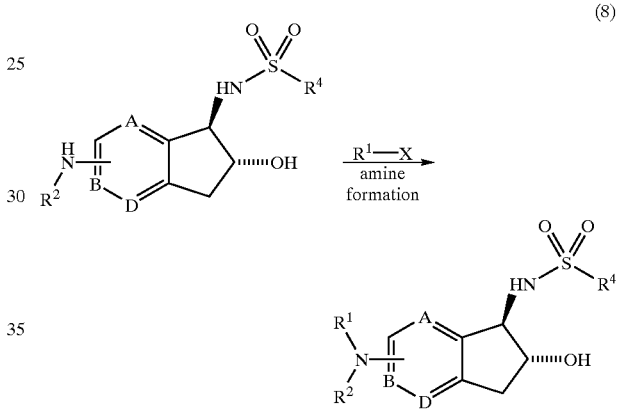

The X substituent in the reagent of step (9) also could be a moiety that permits further substitution on the heteroaryl reagent, such as a nitro ($NO_2$) group, which leads to the following chemistry (nitro reduction (e.g., $SnCl_2$) followed by acylation with an acid chloride to give an amide) according to steps (10) and (11). When the X substituent in the heteroaryl reagent of step (9) is a carboxylic acid moiety, it can be further functionalized by reaction with an amine according to step (12) to give an amide. One skilled in the art will recognize that there are a variety of amide coupling procedures known in the literature.

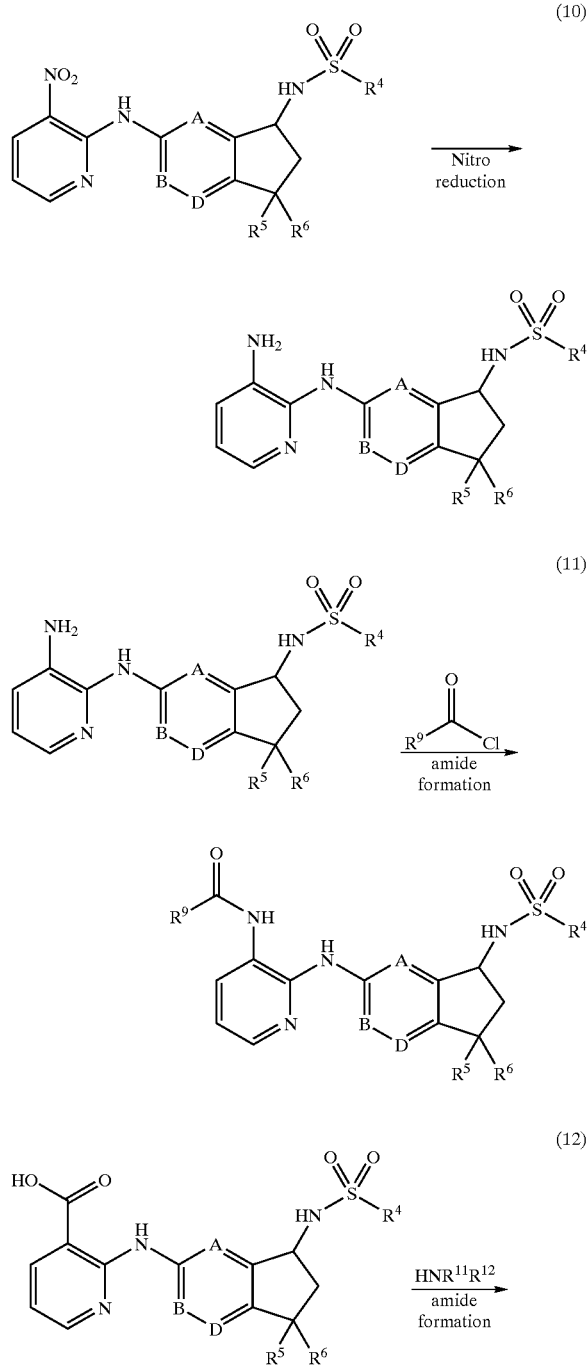

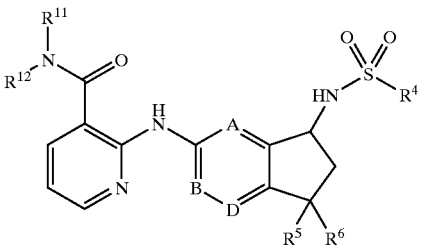

Those skilled in the art will appreciate additional techniques and raw materials suitable for preparing other compounds falling within the scope of the present invention, as illustrated in the subsequent specific examples. For instance, the skilled worker will readily appreciate the option of choosing appropriately substituted raw material and the advantage of employing protecting groups, and will readily understand their application in a specific synthetic approach to improve the yield of desired products having specific substituents.

As noted above and as those skilled in the art of medicinal chemistry well understand, the various synthetic schemes are conducted with raw materials having a combination of suitable substituents selected in order to provide a stable compound structure. Thus, particular substituents and groups of substituents are chosen such that compound stability is obtained and preserved.

It is recognized that there is generally at least one and often more than one chiral center in the compounds falling within the scope of the present invention and thus such compounds will exist as various stereoisomeric forms. Applicants intend to include all the various stereoisomers within the scope of the invention. Thus, this invention is intended to include the cis and trans isomers and the corresponding enantiomers of the compounds of formula I–V. Though the compounds may be prepared as racemates and can conveniently be used as such, individual enantiomers also can be isolated or preferentially synthesized by known techniques if desired. Such racemates and individual enantiomers and mixtures thereof are intended to be included within the scope of the present invention.

The present invention also encompasses the pharmaceutically acceptable prodrugs of the compounds of Formula I. A prodrug is a drug which has been chemically modified and may be biologically inactive at its site of action, but which is degraded or modified by one or more enzymatic or other in vivo processes to the parent bioactive form. Generally, a prodrug has a different pharmacokinetic profile than the parent drug such that, for example, it is more easily absorbed across the mucosal epithelium, it has better salt formation or solubility and/or it has better systemic stability (e.g., an increased plasma half-life).

Those skilled in the art recognize that chemical modifications of a parent drug to yield a prodrug include: (1) terminal ester or amide derivatives which are susceptible to being cleaved by esterases or lipases; (2) terminal peptides which may be recognized by specific or nonspecific proteases; or (3) a derivative that causes the prodrug to accumulate at a site of action through membrane selection, and combinations of the above techniques. Conventional procedures for the selection and preparation of prodrug derivatives are described in H. Bundgaard, Design of Prodrugs, (1985). Those skilled in the art are well-versed in the preparation of prodrugs and are well-aware of its meaning.

The compounds of the present invention can be used in their neat form or in the form of pharmaceutically-acceptable salts derived from inorganic or organic acids, or in the form of their esters, amides, complexes, chelates, hydrates, stereoisomers, crystalline or amorphous forms, metabolites, metabolic precursors, or prodrugs. In the practice of the present invention, compounds of the present invention in their neat form will generally have a molecular weight of 800 or below, usually 600 or below.

Examples of acids which maybe employed to form pharmaceutically acceptable acid addition salts of compounds of the present invention include such inorganic acids as hydrochloric acid, sulphuric acid and phosphoric acid and such organic acids as maleic acid, succinic acid and citric acid. These salts thus include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, pamoate, pectinate, persulfate, 3-phenylpropionate, picrate, pivalate, propionate, succinate, tartrate, thiocyanate, p-toluenesulfonate and undecanoate.

Also, the basic nitrogen-containing groups can be quaternized with such agents as lower alkyl halides, such as methyl, ethyl, propyl, and butyl chlorides, bromides and iodides; dialkyl sulfates, like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil soluble or dispersible products are thereby generally obtained.

The pharmaceutically acceptable salts of the compounds of the present invention also can exist as various solvates, such as with water, methanol, ethanol, dimethylformamide, ethyl acetate and the like. Mixtures of such solvates also can be prepared. Such solvates are within the scope of the present invention.

The pharmacological profile of the potassium channel inhibitory activity of the compounds of the present invention can be readily assessed by those skilled in the art using routine experimentation, such as the procedures and techniques illustrated in the examples which follow. Assays for assessing the activity of particular compounds may employ cells stably transfected to express a specific potassium channel, as well as native mammalian cells. In particular, stable transfected cells, transfected to express a specific potassium channel, which have been treated with a voltage dependent fluorescent dye, such as bis-(1,3-dibutylbarbituric acid) trimethine oxonol, can be used to gauge the inhibitory activity of potassium channel inhibitor compounds, possibly in comparison to known inhibitors. Alternatively, such cells can be primed with a detectible species, such as 86Rb, and then challenged with a particular compound, under conditions otherwise suitable for activating the potassium channel, to assess the potassium inhibitory activity of the compound. The potassium channel inhibitory activity of a compound also can be determined using isolated mammalian cells and the whole cell configuration of the known patch clamp technique (Hamill et al., Pflugers Archiv 391:85, 1981). These and other known techniques can be readily employed by those skilled in the art to assess the activity level of the potassium channel inhibitor compounds of the present invention.

The compounds of the present invention may be administered by a variety of routes including orally, parenterally, sublingually, intranasally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intracardiac injection, or infusion techniques. Topical administration may also involve the use of transdermal administration such as transdermal patches or iontophoresis devices.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,2-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound maybe admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The compounds of the present invention can also be administered in the form of liposomes. As is known in the art, liposomes are generally derived from phospholipids or other lipid substances. Liposomes are formed as mono- or multi-lamellar hydrated liquid crystals that are dispersed in an aqueous medium. Any non-toxic physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33, et seq.

To select preferred compounds from less preferred compounds, one uses by example the in vitro assays detailed under the sub-heading BioAssays hereafter described. Typically, a preferred compound will produce half maximal blocking activity at a concentration below about 5 $\mu$M, preferably below about 1 $\mu$M, more preferably below about 100 nM and most preferably below about 10 nM in the in vitro assays described. One of ordinary skill will recognize that the final and optimum dose and regimen will be determined empirically for any given drug.

Total daily dose administered to a host in single or divided doses may be an amount, for example, from 0.001 to 100 mg of active ingredient per kg body weight on a daily basis and more usually 0.01 to 10 mg/kg/day. Dosage unit compositions may contain such amounts of submultiples thereof to make up the daily dose. It is anticipated that a therapeutically effective serum concentration of active ingredient will be 10 nM to 10 $\mu$M (5 ng/ml to 5 $\mu$g/ml).

The amount of active ingredient that may be combined with carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, and diet of the patient, the time of administration, the route of administration, the rate of excretion, whether a drug combination is used, and the severity of the particular disease.

Using the processes described hereinabove, the following compounds (each assigned a unique number identifier) can be synthesized:

1
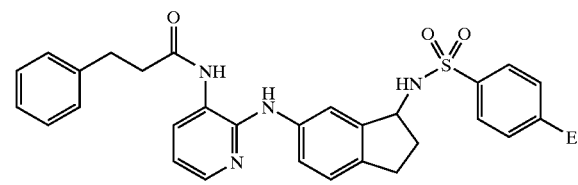

2
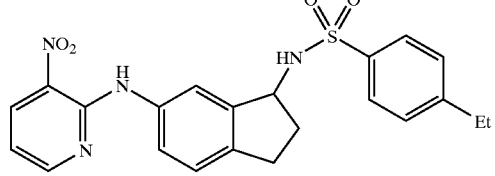

3
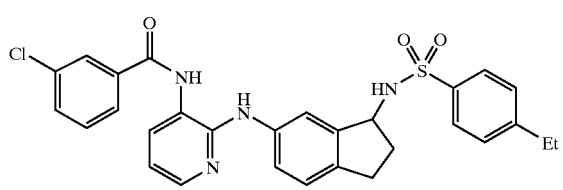

4
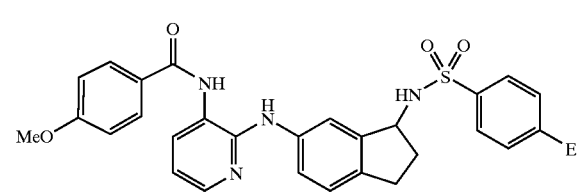

5
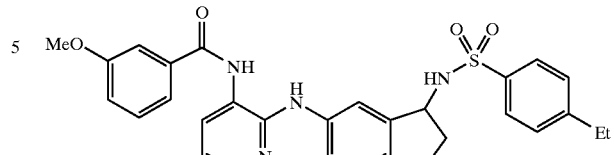

6
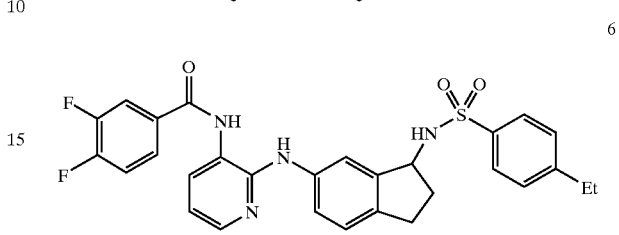

7
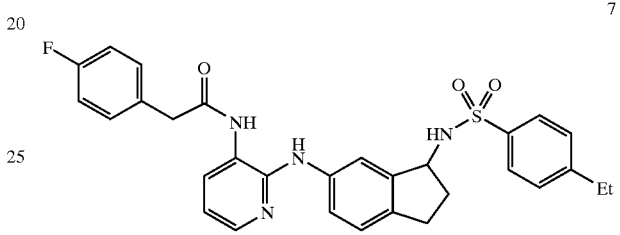

8
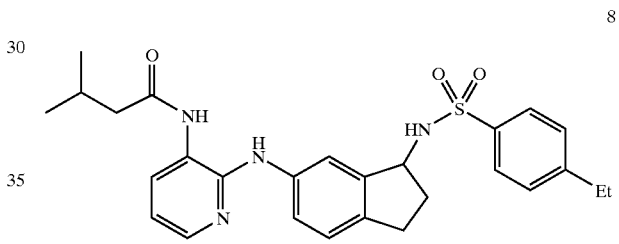

9
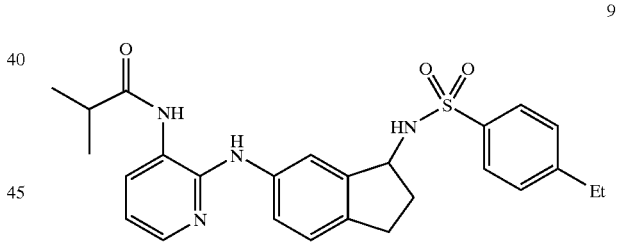

10
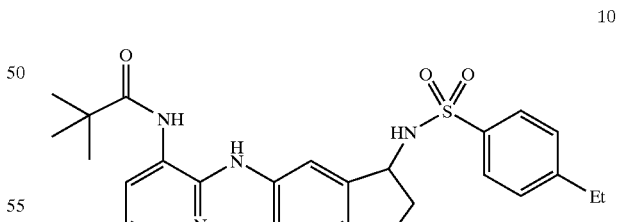

11
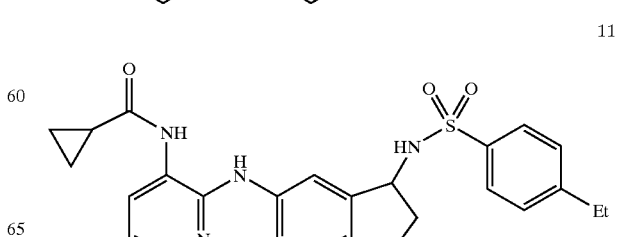

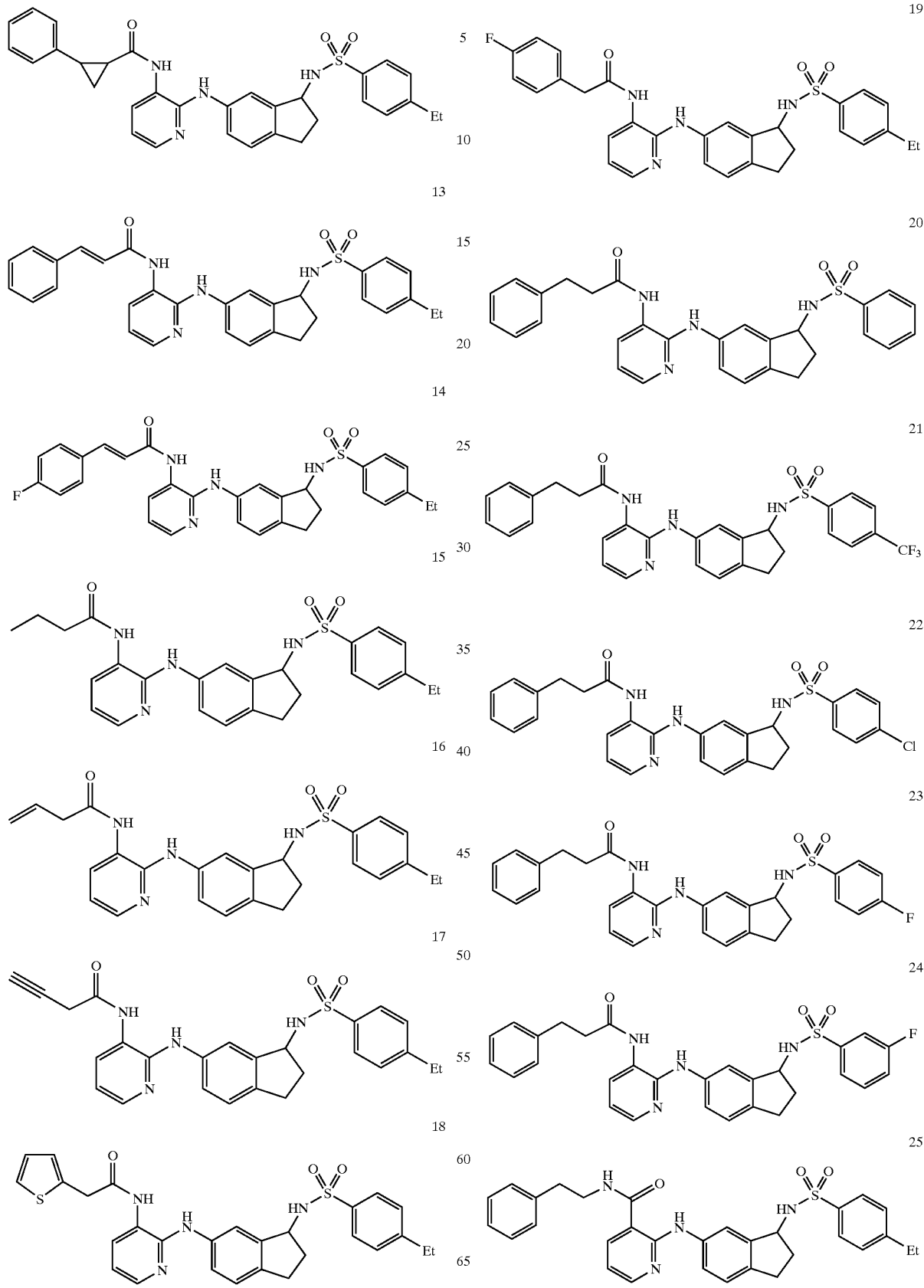

-continued

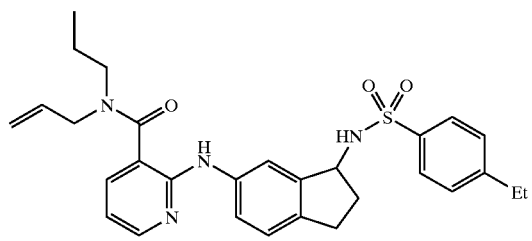
55
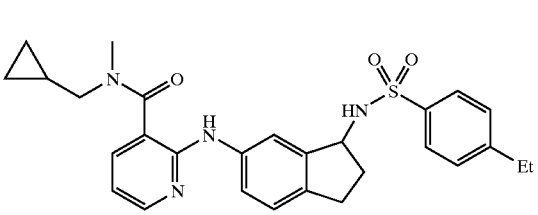
56
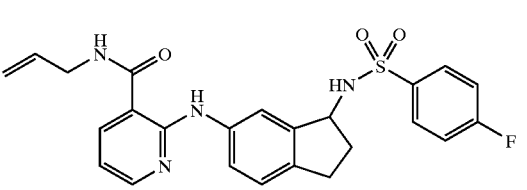
57
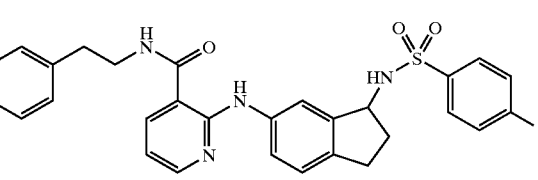
58
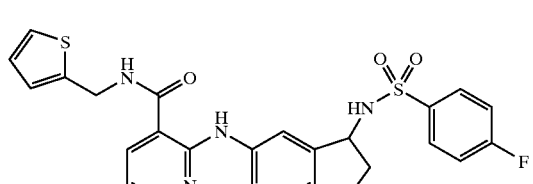
59
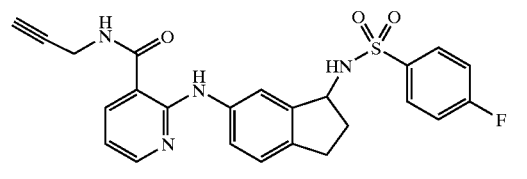
60
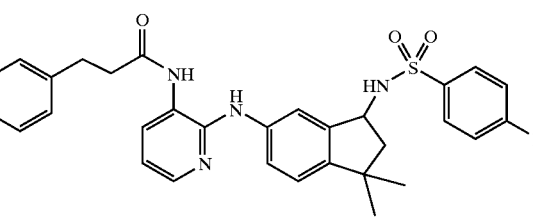
61
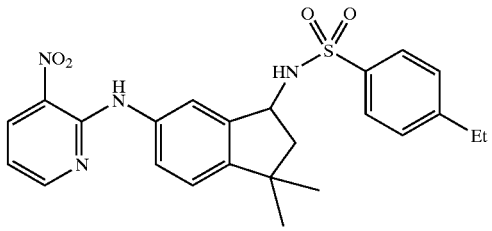
62
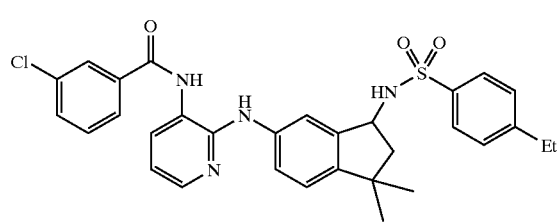
63
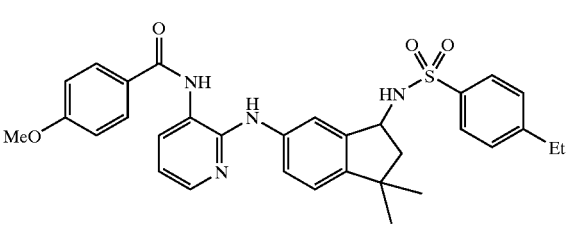
64
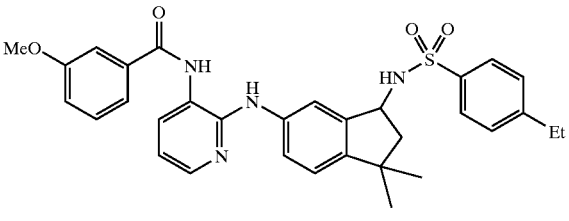
65
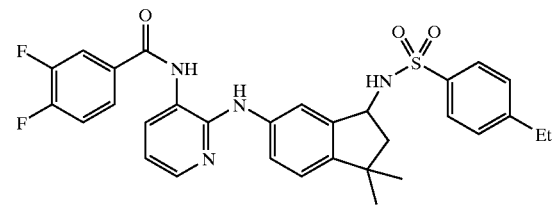
66
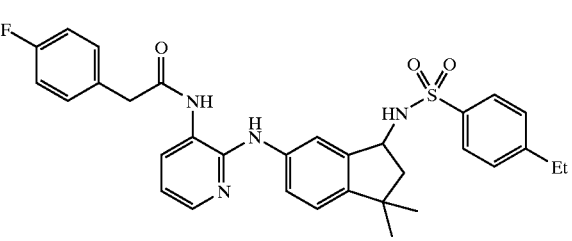
67

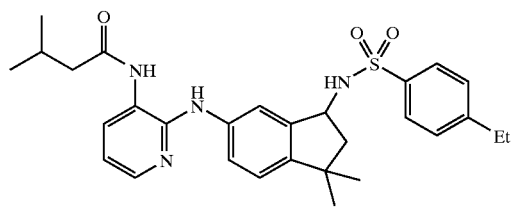
68
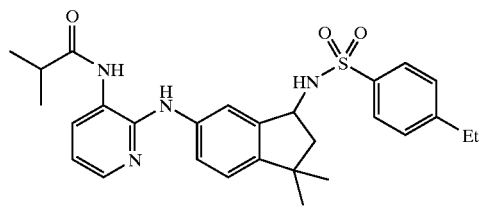
69
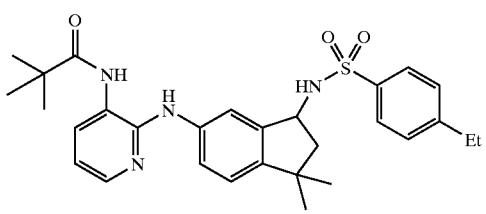
70
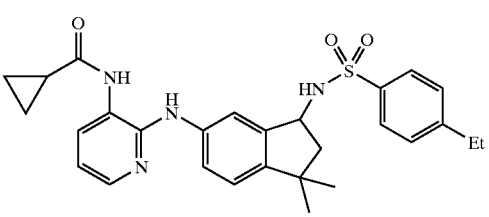
71
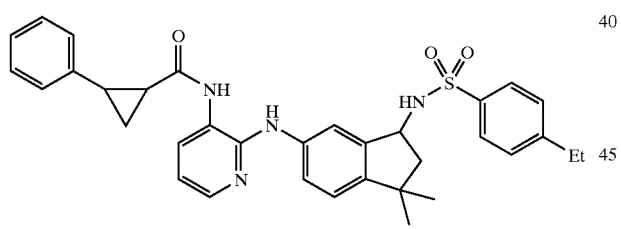
72
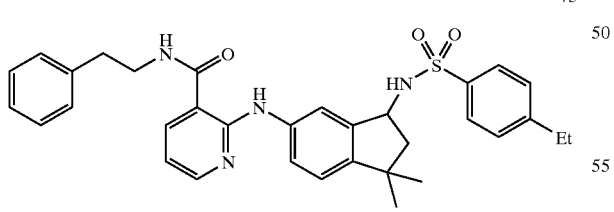
73
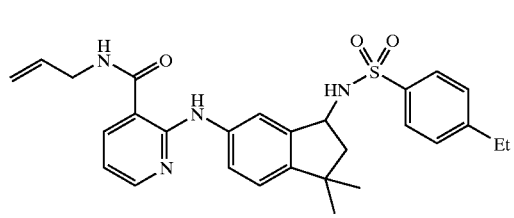
74
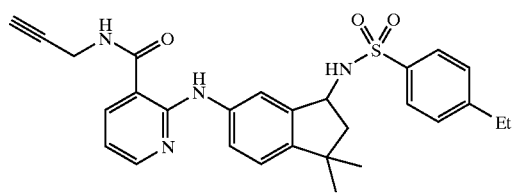
75
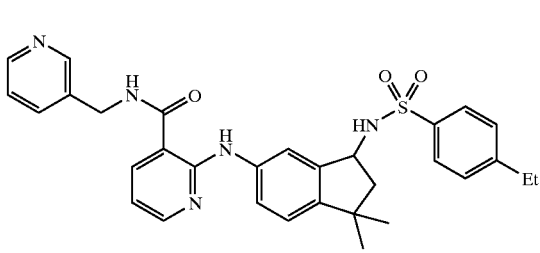
76
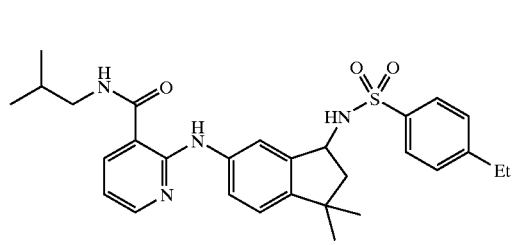
77
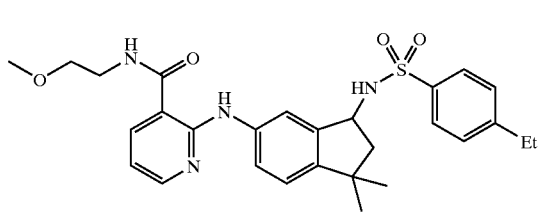
78
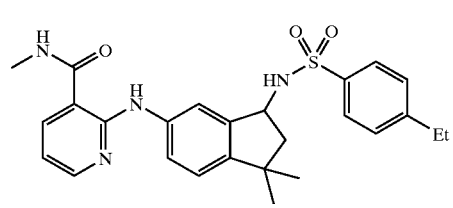
79
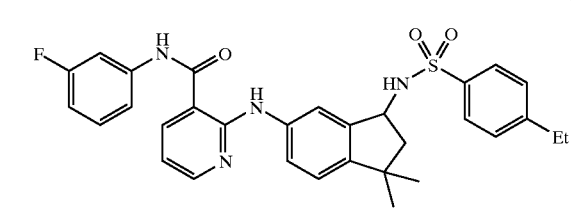
80
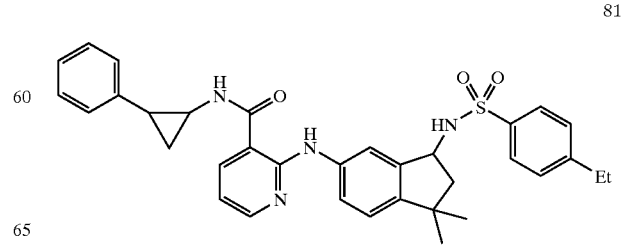
81

82
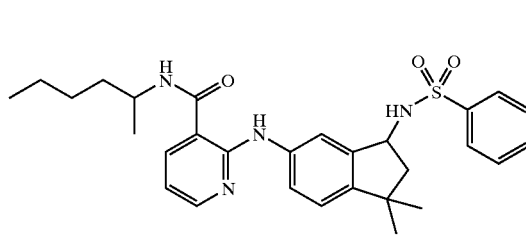
83
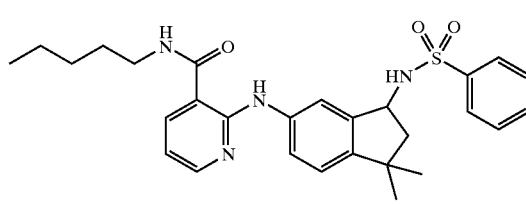
84
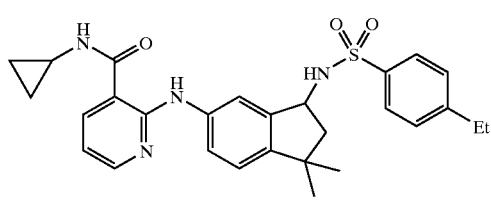
85
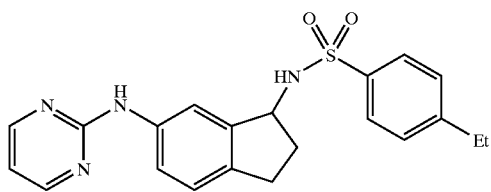
86
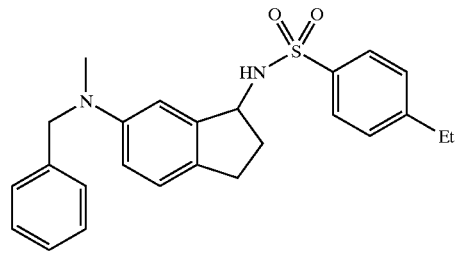
87
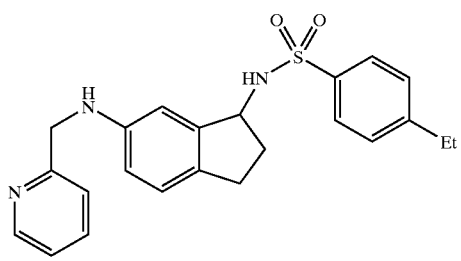
88
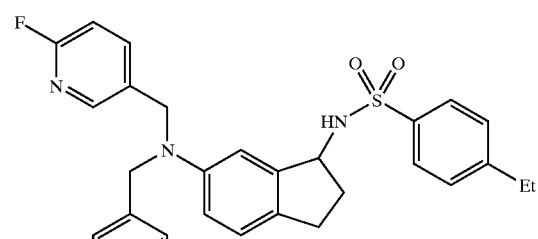
89
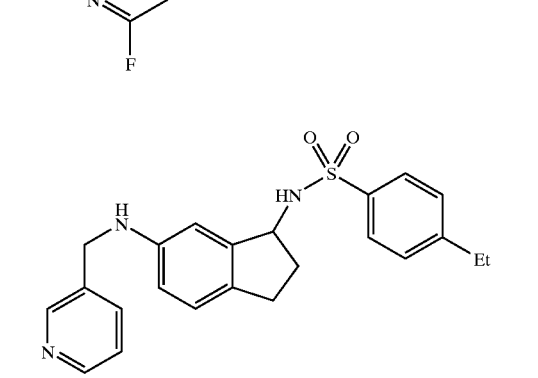
90
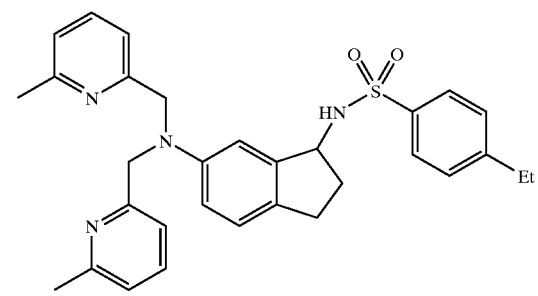
91
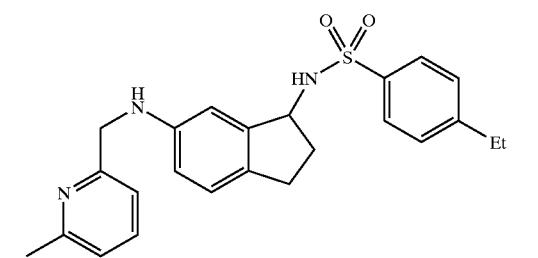
92
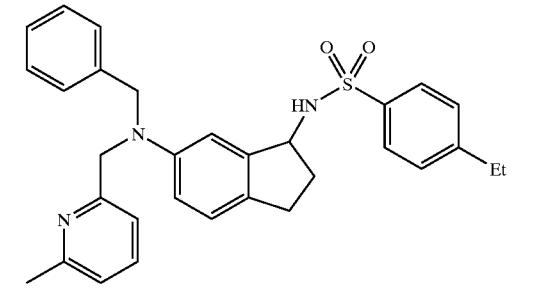

93
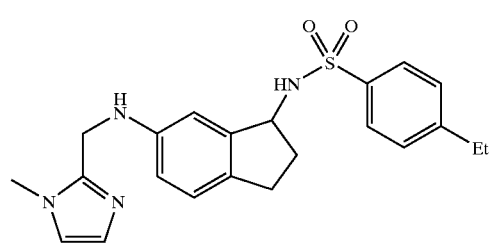
94
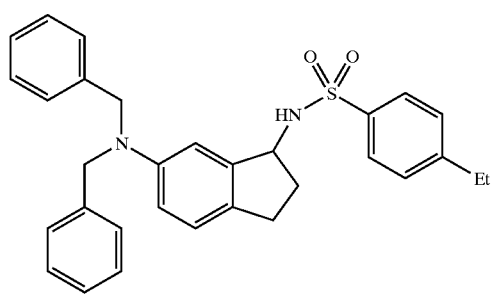
95
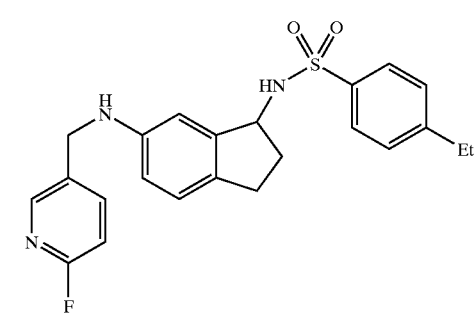
96
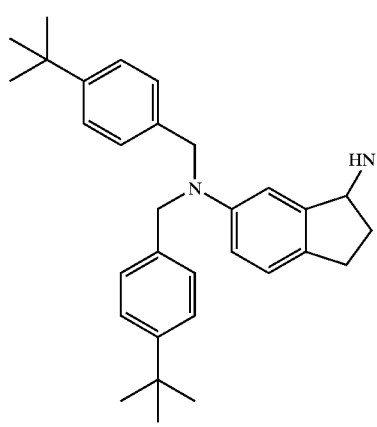
97
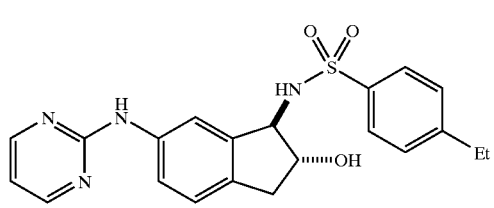
98
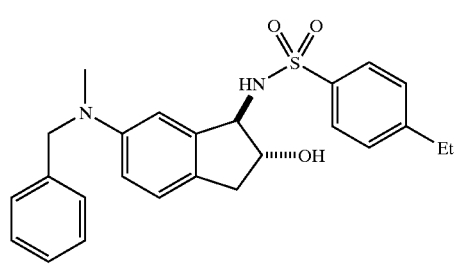
99
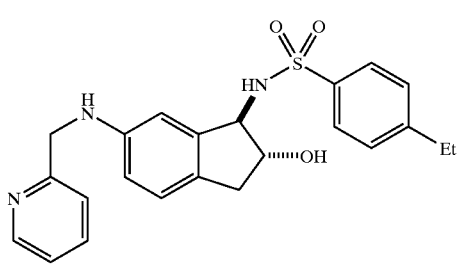
100
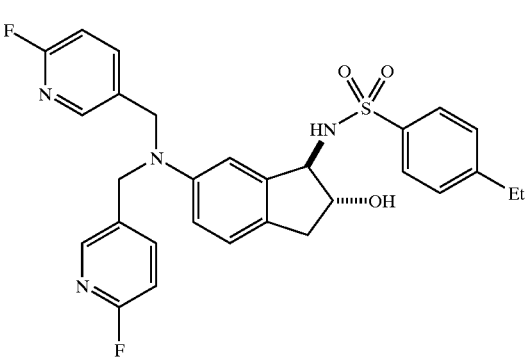
101
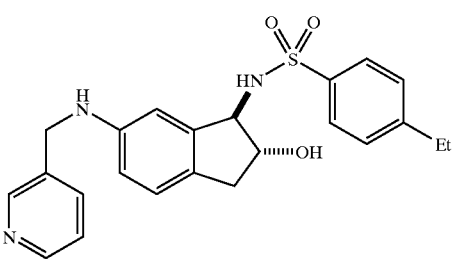
102
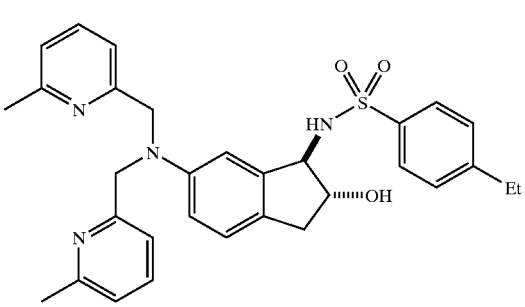

103 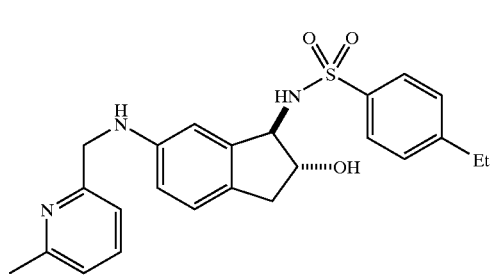
104 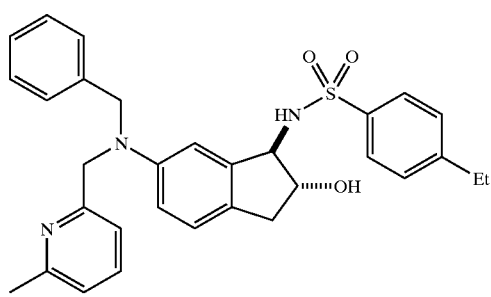
105 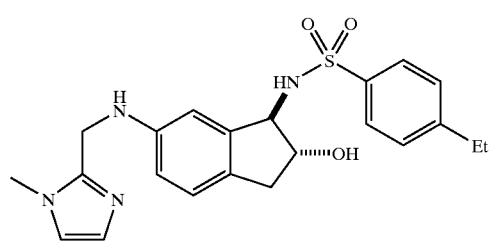
106 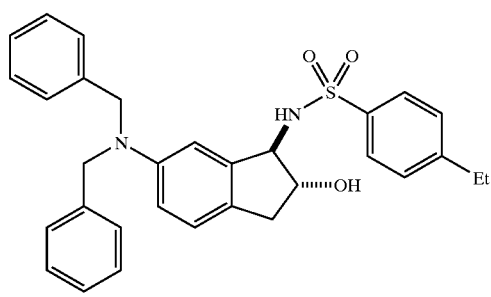
107 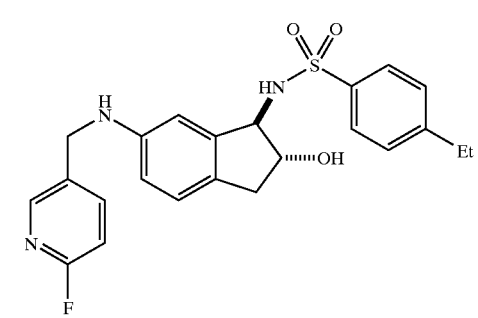
108 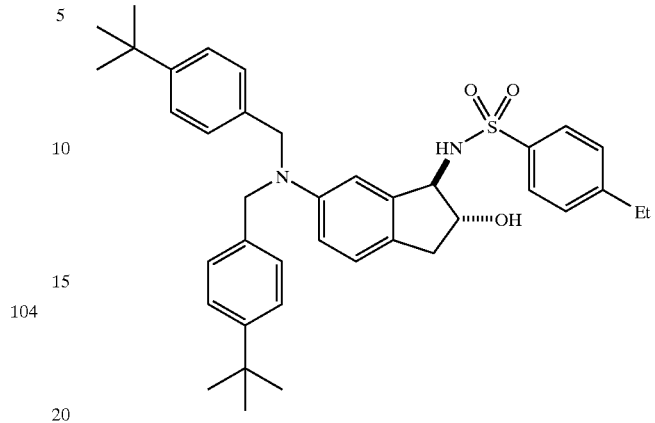
109 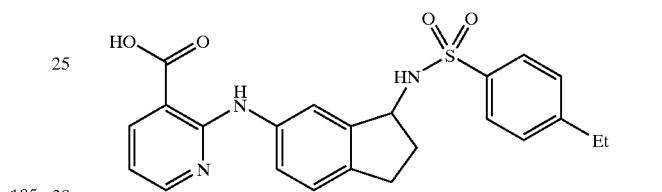
110 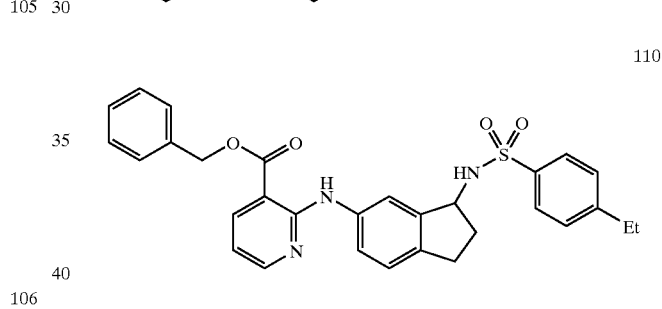
111 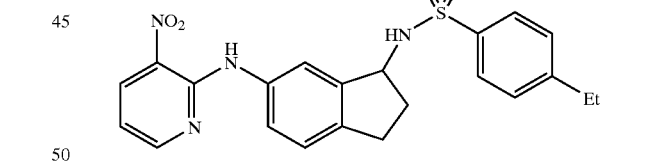
112 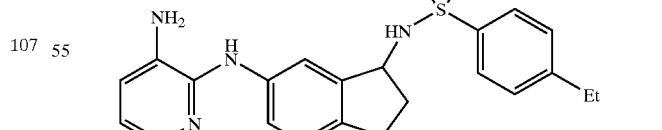
113 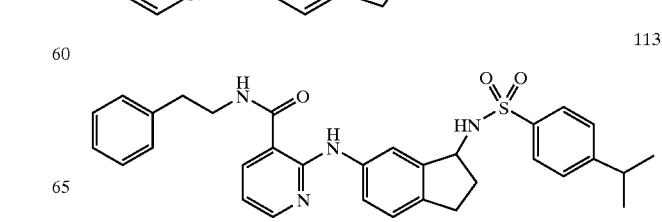

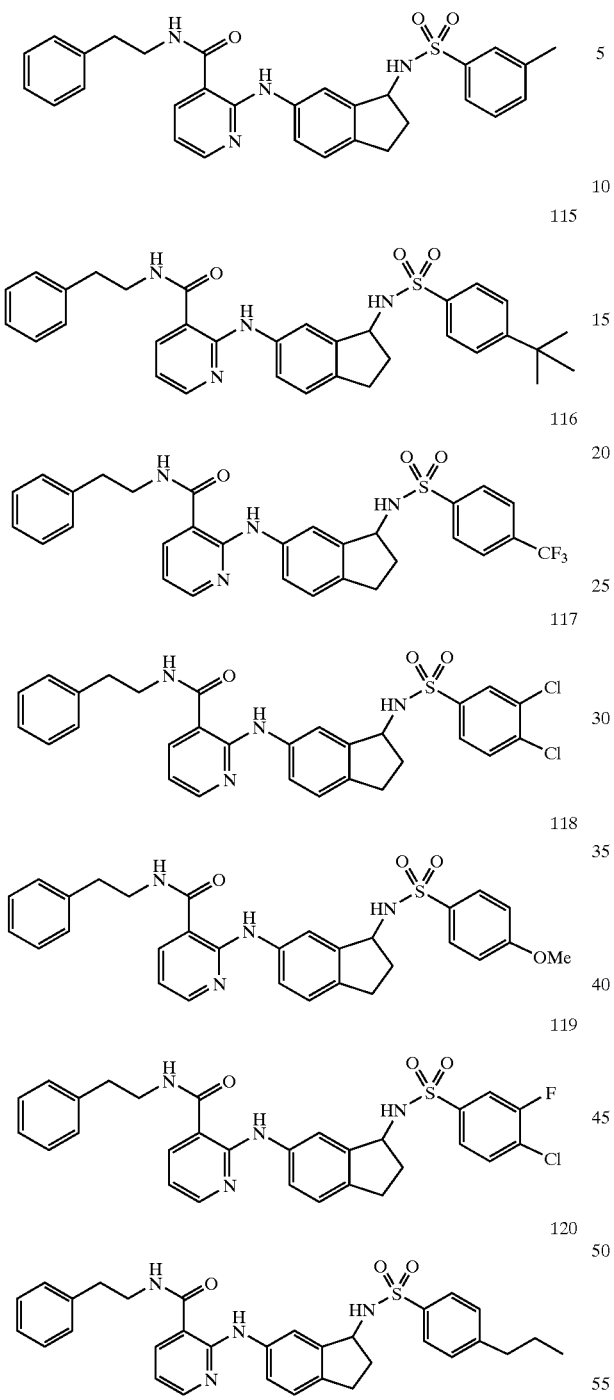

The present invention is further explained in greater detail in the Examples which follow. These experimental examples are intended as illustrative of the invention, and are not to be taken as limiting thereof. Unless otherwise indicated, all references to parts and percentages are based on weight and all temperatures are expressed in degrees Celsius. The scope of the invention is not construed as merely consisting of the following examples.

EXAMPLES

Compound Preparation

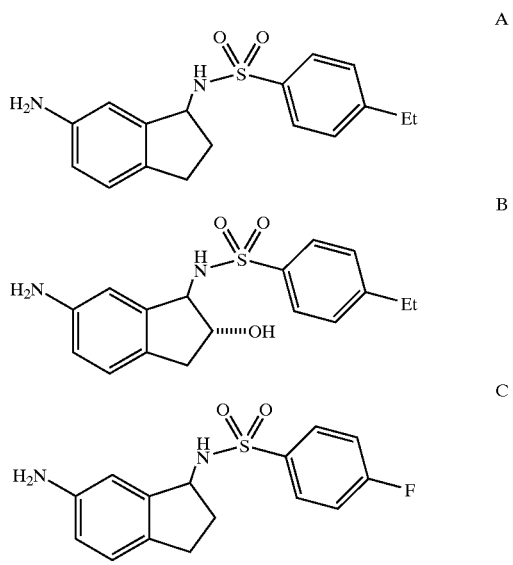

Compounds A, B and C and related amino indanes can be prepared as described in N. Castle et al WO9804521 (U.S. Pat. No. 6,083,986); D. Buckle et al *J Med. Chem.* 1991, 34, 919–926 (and references cited therein) and J. Tedder et al., EP0321175.

Separation of the enantiomers of compound A and compound B can be accomplished by chiral HPLC using a Chiralpak AS column (Chiral Technologies, Inc.) for compound A and compound C and a Chiralpak OJ column (Chiral Technologies, Inc.), for compound B. Asymmetric synthetic methods can also be used to separate the enantiomers of compounds A, B and C. For example, see N. Castle et al., WO 98/04521 (See also U.S. Pat. No. 6,083,986 incorporated herein by reference).

Example 1
Preparation of Compound 93

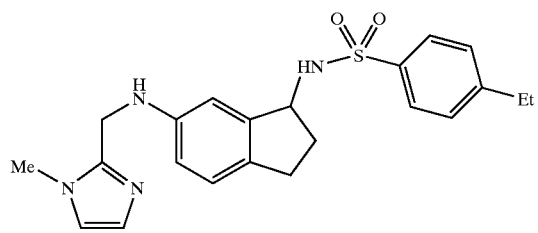

To a stirred solution of Compound A (200 mg, 0.948 mmol) in methanol (5 mL) at room temperature was added 1-methyl-2-imidazolecarboxaldehyde (125 mg, 1.13 mmol) and anhydrous sodium sulfate (673 mg, 4.74 mmol). The reaction mixture was heated at 50° C. for six hours under nitrogen. The excess sodium sulfate was filtered from the reaction mixture while it was still warm and the filtrate was cooled to room temperature. Sodium borohydride (103 mg, 2.72 mmol) was added to the filtrate and it was stirred for 15 hours at room temperature. The solution was quenched with saturated aqueous sodium bicarbonate solution and the methanol was removed by rotary evaporation. The resulting mixture was diluted with water and extracted with ethyl acetate. The organic layer was dried over anhydrous sodium sulfate, filtered, and concentrated. The residue was recrystallized from a minimum amount of hot ethyl acetate to give Compound 93 (229 mg, 59%) as a white solid. The mother liquor was concentrated and subjected to flash column chromatography on silica gel using 9:1 ethyl acetate:methanol as the eluent to provide additional Compound 93 (39 mg). $^1$H NMR (300 MHz, d$_6$-acetone) δ (ppm) 7.90 (d, 2 H, J=8.2 Hz), 7.47 (d, 2 H, J=8.1 Hz), 6.99 (s, 1 H), 6.92 (d, 1 H, J=8.2 Hz), 6.82 (d, 1 H, J=0.8 Hz), 6.67 (dd, 1 H, J=2.0, 8.1 Hz), 6.50 (s, 1 H), 5.14 (s, 1 H), 4.70 (m, 2H), 4.21 (s, 2H), 3.70 (s, 3H), 2.75, (q 2H, J=7.6 Hz), 2.67 (dd, 1 H, J=3.3, 8.9 Hz), 2.56 (m, 1 H), 2.12 (m, 1 H), 1.69 (m, 1 H), 1.25 (t, 3H, J=7.6 Hz). $^{13}$C NMR (75 MHz, d$_6$-acetone) δ (ppm): 149.4, 147.4, 145.8, 143.4, 139.4, 131.5, 128.3, 126.9, 125.6, 124.6, 121.8, 113.5, 108.1, 58.7, 40.4, 34.2, 31.9, 28.5, 28.3, 14.3.

The following compounds in Example 2 and Example 3 were synthesized using the procedures described in Example 1 using Compound A and the appropriate aldehyde.

Example 2
Preparation of Compound 89

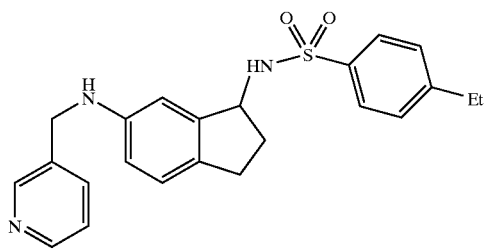

Compound 89 was obtained by reacting Compound A with 3-pyridine carboxaldehyde under the reaction conditions described in Example 1 in 78% yield. Purification was accomplished by flash column chromatography on silica gel using 6:2:2 ethyl acetate:dichloromethane:hexanes as the eluent. $^1$H NMR (300 MHz, CDCl$_3$) δ (ppm): 8.47 (s, 1 H), 8.45 (d, J=4.8 Hz, 1 H), 7.81 (d, J=8.1 Hz, 2H), 7.63 (d, J=7.8 Hz, 1 H), 7.31 (d, J=8.1 Hz, 2 H), 7.26–7.20 (m, 1 H), 6.94 (d, J=8.1 Hz, 1 H), 6.45 (d, J=7.8 Hz, 1 H), 6.41 (s, 1 H), 5.43 (s, J=9.0 Hz, 1 H), 4.73 (q, J=7.8 Hz, 1 H), 4.19 (s, 2H), 2.78–2.54 (m, 4H), 2.30–2.20 (m, 1 H), 1.73–1.61 (m, 1 H), 1.23 (t, J=7.5 Hz, 3H);. $^{13}$C NMR (75 MHz, CDCl$_3$) δ (ppm): 149.5, 149.0, 148.6, 147.0, 143.6, 138.7, 135.4, 134.9, 132.1, 128.6, 127.2, 125.4, 123.6, 113.6, 108.4, 58.9, 46.0, 35.0, 29.1, 28.8, 15.2

Example 3
Preparation of Compound 91

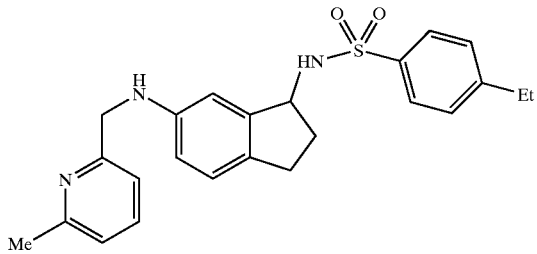

Compound 91 was obtained by reacting Compound A with 6-methyl-2-pyridine carboxaldehyde under the reaction conditions described in Example 1 in 66% yield. Purification was accomplished by recrystallization from ethyl acetate/hexane. $^1$H NMR (300 MHz, CDCl$_3$) δ (ppm): 7.81 (d, J=7.8 Hz, 2 H), 7.50 (t, J=7.8 Hz, 1 H), 7.31 (d, J=7.8 Hz, 2H), 7.06 (d, J=7.02 (d, J=7.8 Hz, 1 H), 6.92 (d, J=8.4 Hz, 1 H), 6.50 (d, J=7.8, 1 H), 6.38 (s, 1 H), 5.10 (d, J=8.7 Hz, 1 H), 4.72 (q, J=7.5 Hz, 1 H), 4.24 (s, 2 H), 2.70 (q, J=7.2 Hz, 2H), 2.63–2.56 (m, 2H), 2.56 (s, 3H), 2.25–2.22 (m, 1H), 1.71–1.62 (m, 1H), 1.24 (t, J=7.2 Hz, 3H); $^{13}$C NMR (75 MHz, CDCl$_3$) δ (ppm): 158.0,157.5,149.4,147.4,143.3, 138.6, 136.9, 131.4, 128.6, 127.3, 125.2, 121.7, 118.7, 113.8, 108.3, 58.9, 49.4, 35.0, 29.1, 28.8, 24.5, 15.2.

Example 4
Preparation of Compound 101

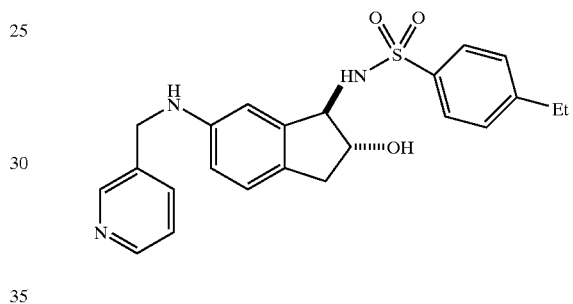

To a stirred solution of Compound B (294 mg, 0.88 mmol) in methanol (10 mL) at room temperature was added 3-pyridine carboxaldehyde (0.12 mL, 1.27 mmol) followed by anhydrous sodium sulfate (480 mg, 3.38 mmol). The reaction mixture was heated at 55° C. for 24 hours under nitrogen at which time thin layer chromatography (TLC) analysis indicated that no starting material remained. The reaction was cooled to 0° C. and treated with sodium borohydride (53 mg, 1.40 mmol) in one portion. After 15 minutes at 0° C., the cooling bath was removed and the reaction was stirred at room temperature for three hours. The methanol was removed by rotary evaporation and the residue was treated with ethyl acetate and water. The organic layer was separated, washed with saturated sodium chloride solution, dried over anhydrous sodium sulfate, filtered and concentrated. The residue was purified by flash column chromatography on silica gel using 8:1:1 ethyl acetate:hexane:acetonitrile as the eluent to provide Compound 101 (197 mg, 53%) as a white foam. $^1$H NMR (300 MHz, CDCl$_3$) δ (ppm): 8.41 (S, 1 H), 8.33 (d, J=4.2 HZ, 1 H), 7.82 (d, J=8.1 Hz, 2H), 7.57 (d, J=7.8 Hz, 1 H), 7.25 (d, J=8.1 Hz, 2H), 7.16 (dd, J=4.8 and 7.5 Hz, 1 H), 6.86 (d, J=8.1 Hz, 1 H), 6.59 (d, J=7.8 Hz, 1 H), 6.41 (d, J=6.9 Hz, 1 H), 6.20 (s, 1 H), 3.95 (t, J=6.9 Hz, 1 H, 4.30 (q, J=7.5 Hz, 1 H), 4.11 (s, 2H), 3.92 (broad s, 1 H), 3.01 (dd, J=7.5 and 15.3 Hz, 1 H), 2.67–2.60 (m, 3H), 1.19 (t, J=7.5 Hz, 3H); $^{13}$C NMR (75 MHz, CDCl$_3$) δ (ppm): 149.7, 148.7, 148.2, 147.3, 140.2, 137.6, 135.5, 135.1, 128.7, 128.3, 127.4, 125.7, 123.7, 113.7, 108.2, 80.8, 65.6, 45.8, 37.0, 28.8, 15.2.

Example 5
Preparation of Compound 85

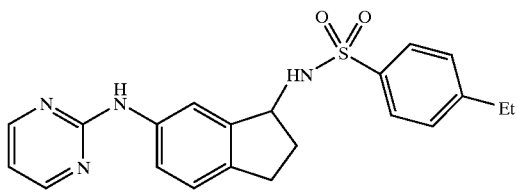

To a solution of Compound A (100 mg, 0.32 mmol) in 1-methyl-2-pyrrolidinone (0.7 mL) at room temperature was added 2-chloropyrimidine (40 mg, 0.35 mmol). The reaction mixture was heated at 140° C. for 21 hours. The crude reaction mixture was directly subjected to flash column chromatography on silica gel eluting with hexane:ethyl acetate (3:2 then 1:1) to give Compound 85 (49 mg, 39%) as a white solid. $^1$H NMR (300 MHz, CDCl$_3$) δ (ppm): 8.33 (2 H, d, J=4.9 Hz), 7.87 (2H, d, J=8.3 Hz), 7.40 (1 H, dd, J=1.9, 8.0), 7.33 (2 H, d, J=8 Hz), 7.31 (1 H, s), 7.14 (1 H, d, J=8.2 Hz), 6.69 (1 H, t, J=4.8), 5.18 (1 H, d, J=8.9 Hz), 4.83 (1 H, q, J=8.4 Hz), 2.91–2.81 (1 H, m), 2.74–2.64 (1 H, m), 2.71 (2 H, q, J=7.7 Hz), 2.41–2.31 (1 H, m), 1.87–1.72 (2 H, m), 1.25 (3 H, t, J=7.7 Hz).

Example 6
Preparation of Compound 109

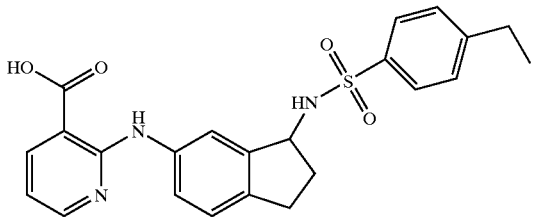

The aniline compound A (100 mg, 0.316 mmol), 2-chloronicotinic acid (87 mg, 0.553 mmol), potassium carbonate (109 mg, 0.790 mmol) and copper (I) bromide (5.0 mg, 0.032 mmol) were combined in 0.5 mL N,N-dimethylformamide in a closed vial containing a stir bar. The reaction mixture was stirred and heated to 150° C. and held for three hours. The reaction mixture was cooled to room temperature and more copper (I) bromide (18 mg, 0.13 mmol) was added. The vial was again sealed and the reaction heated to 150° C. and held for another two hours. The vial was cooled to room temperature and 1 mL 1N hydrochloric acid was added. This mixture was stirred for ten minutes, filtered, and washed with water and methanol. The methanol was removed from the filtrate by rotary evaporation and the remaining aqueous solution was extracted with ethyl acetate. The organic layers were combined and dried over sodium sulfate. Compound 109 (55 mg, 40%) was obtained as a yellow foam after two flash column chromatography purifications using 3:1:1 ethyl acetate: methylene chloride: hexanes followed by ethyl acetate as the eluents: $^1$HNMR (300 MHz acetone-d$_6$) δ10.56 (broad s, 1H), 8.36 (d, 1H, J=6.1 Hz), 8.27 (broad s, 1H), 7.97 (s, 1H), 7.87 (d, 2H, J=7.9 Hz), 7.53 (m, 1H), 7.41 (d, 2H, J=8.4 Hz), 7.01 (m, 1H), 6.86 (d, 1H, J=8.5 Hz), 6.74 (broad s, 1H), 4.76 (m, 1H), 2.69 (m, 4H), 2.16 (m, 1H), 1.71 (m, 1H), 1.21 (t, 3H, J=7.6 Hz). $^{13}$C NMR (75 MHz, acetone-d$_6$) δ (ppm): 170.1, 162.5, 156.1, 149.1, 144.9, 143.0, 141.2, 139.8, 136.4, 128.5, 127.1, 124.5, 120.7, 116.3, 113.1, 58.8, 35.5, 34.4, 30.3, 14.8.

Example 7
Preparation of Compound 26

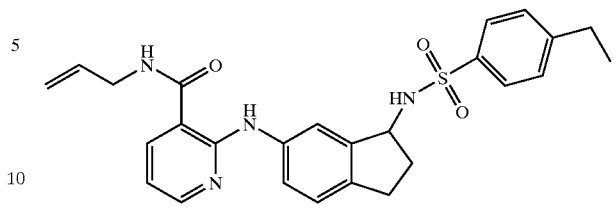

The carboxylic acid Compound 109 (50 mg, 0.114 mmol), N,N'-dicyclohexylcarbodiimide (29 mg, 0.126 mmol), N-hydroxysuccinimide (16 mg, 0.137 mmol) were combined in 1.0 mL of tetrahydrofuran and stirred at room temperature for five hours. The dicyclohexyl urea produced during the reaction was then removed by filtration through a small plug of silica gel, which was washed with 0.5 mL of tetrahydrofuran. The filtrate was then combined with allylamine (7 mg, 0.13 mmol) and the reaction mixture was stirred at room temperature for 18 hours. Saturated aqueous sodium bicarbonate was added and the resulting mixture was extracted with ethyl acetate. The organic layer was dried over sodium sulfate. Compound 26 (32 mg, 59%) was obtained as a white foam after flash column chromatography using 1:1:1 mixture of ethyl acetate: methylene chloride: hexanes as the eluent: $^1$H NMR (acetone-d$_6$ 300 MHz) δ (ppm): 10.88 (s, 1H), 8.28 (dd, 1H, J=1.9, 4.8 Hz), 8.16 (broad s, 1H), 8.11 (dd, 1H, J=1.9, 7.8 Hz), 7.90 (d, 2H, J=8.4 Hz), 7.65 (dd, 1H, J=1.8, 8.2 Hz), 7.45 (d, 2H, J=8.3 Hz), 7.37 (s, 1H), 7.09 (d, 1H, J=8.2 Hz), 6.84 (d, 1H, J=8.9 Hz), 6.78 (dd, 1H, J=4.8, 7.7 Hz), 6.00 (m, 1H), 5.26 (dd, 1H, J=1.5, 17.3 Hz), 5.12 (dd, 1H, J=1.5, 10.3 Hz), 4.78 (m, 1H), 4.06 (m, 2H), 2.94–2.61 (m, 4H), 2.22 (m, 1H), 1.79 (m, 1H), 1.24 (t, 3H, J=7.5 Hz). $^{13}$C NMR (acetone-d$_6$ 75 MHz) δ (ppm): 167.9, 155.4, 150.8, 149.1, 143.2, 140.0, 139.5, 136.2, 135.9, 134.9, 128.5, 127.1, 124.4, 119.8, 115.7, 115.2, 112.9, 110.9, 58.8, 41.9, 34.6, 29.1, 28.4, 14.8.

Example 8
Preparation of Compound 42

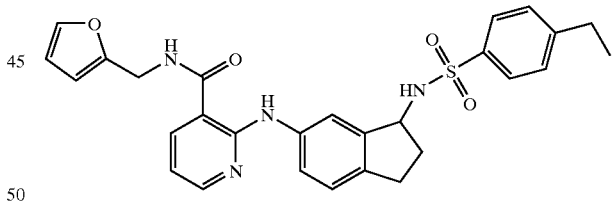

Compound 42 was produced as described for compound 26 using furfurylamine instead of allylamine in 66% yield. The aniline compound A (50 mg, 0.114 mmol), dicyclohexylcarbonate (29 mg, 0.126 mmol) and N-hydroxysuccinimide (16 mg, 0.137 mmol) were combined in 1.0 mL of tetrahydrofuran and stirred at room temperature for five hours. The dicyclohexyl urea produced during the reaction was then removed by filtration through a small plug of silica gel, which was washed with 0.5 mL of tetrahydrofuran. The filtrate was then combined with furfurylamine (12 mg, 0.13 mmol) and the reaction mixture was stirred at room temperature for 18 hours. Saturated aqueous sodium bicarbonate was added and the resulting mixture was extracted with ethyl acetate. The organic layer was dried over sodium sulfate. Compound 42 (39 mg, 66%) was obtained as a white foam after flash column chromatography using 1:1:1 mixture of ethyl acetate: methylene chloride: hexanes as the eluent: $^1$H NMR (acetone-$d_6$ 300 MHz) δ (ppm): 10.86 (s, 1H), 8.43 (broad s, 1H), 8.28 (dd, 1H, J=1.8, 4.9 Hz), 8.11 (dd, 1H, J=1.8, 7.9 Hz), 7.90 (d, 2H, J=8.3 Hz), 7.65 (dd, 1H, J=1.8, 8.2 Hz), 7.45 (m, 3H), 7.36 (s, 1H), 7.09 (d, 1H, J=8.1 Hz), 6.84 (d, 1H, J=8.9 Hz), 6.77 (dd, 1H, J=4.8, 7.8 Hz), 6.37 (m, 2H), 4.80 (m, 1H), 4.05 (dd, 2H, J=7.0, 14.2 Hz), 2.93–2.61 (m, 4H), 2.24 (m, 1H), 1.71 (m, 1H), 1.23 (t, 3H, J=7.5 Hz). $^{13}$C NMR (acetone-$d_6$ 75 MHz) δ (ppm): 168.0, 155.4, 152.1, 151.0, 149.1, 143.2, 142.2, 140.0, 139.4, 136.4, 136.0, 128.6, 127.1, 124.5, 119.9, 115.7, 112.9, 110.6, 110.4, 107.3, 58.8, 36.3, 34.6, 29.1, 28.4, 14.8.

Example 9

Preparation of Compound 27

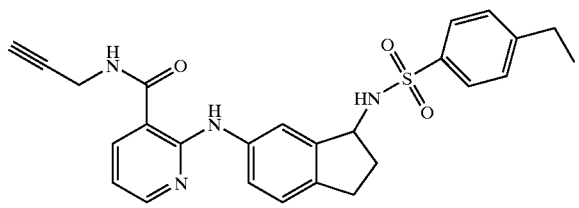

Compound 27 was produced as described for compound 26 using propargylamine instead of allylamine in 71% yield: $^1$H NMR (acetone-$d_6$ 300 MHz) δ (ppm): 10.79 (s, 1H), 8.39 (broad s, 1H), 8.30 (d, 1H, J=3.5 Hz), 8.11 (d, 1H, J=7.0 Hz), 7.90 (d, 2H, J=8.2 Hz), 7.64 (d, 1H, J=8.0 Hz), 7.46 (d, 2H, J=8.2 Hz), 7.34 (s, 1H), 7.10 (d, 1H, J=8.2 Hz), 6.86 (d, 1H, J=8.7 Hz), 6.79 (dd, 1H, J=4.9, 7.6 Hz), 4.80 (m, 1H), 4.92 (d, 1H, J=5.2 Hz), 4.23 (s, 2H), 2.85–2.61 (m, 5H), 1.82 (m, 1H), 1.24 (t, 3H, J=7.5 Hz).

Example 10

Preparation of Compound 37

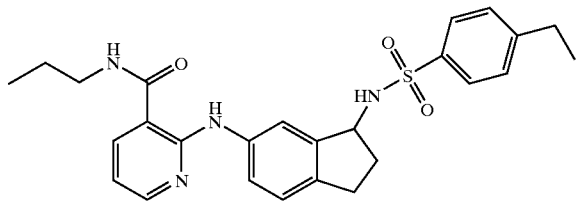

Compound 37 was obtained as described for compound 26 using propylamine instead of allylamine in 62% yield: $^1$H NMR (acetone-$d_6$ 300 MHz) δ (ppm): 10.92 (s, 1H), 8.27 (d, 1H, J=3.7 Hz), 8.04 (d, 1H, J=7.0 Hz), 7.90 (d, 2H, J=8.2 Hz), 7.64 (d, 1H, J=7.4 Hz), 7.46 (d, 2H, J=8.2 Hz), 7.36 (s, 1H), 7.09 (d, 1H, J=8.1 Hz), 6.85 (d, 1H, J=8.9 Hz), 6.76 (dd, 1H, J=4.9, 7.6 Hz), 4.79 (m, 1H), 3.39 (dd, 2H, J=7.8, 12.9 Hz), 2.81–2.61 (m, 5H), 2.24 (m, 1H), 1.80 (m, 1H), 1.65 (sextet, 2H, J=7.2 Hz), 1.24 (t, 3H, J=7.5 Hz), 0.97 (t, 3H, J=7.5 Hz).

Example 11

Preparation of Compound 121

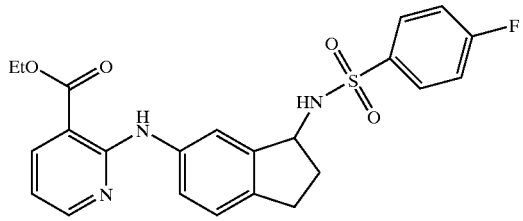

The aniline compound C (200 mg, 0.653 mmol) and ethyl 2-chloronicotinoate (170 mg, 0.899 mmol) were combined in 0.5 mL of dry N,N-dimethylformamide and heated to 150° C. for 6 hours. The mixture was then cooled to room temperature and partitioned between an aqueous solution of 1N hydrochloric acid and ethyl acetate. The layers were separated and the aqueous layer was extracted with ethyl acetate. The organic layers were combined and dried over sodium sulfate. After filtration and rotary evaporation, the residue was purified by flash column chromatography using 2:1 hexanes:ethyl acetate as the eluent. Compound 121 was obtained as an off-white foam (75 mg, 25%): $^1$H NMR (CD$_3$OD 300 MHz) δ (ppm): 8.30 (m, 2H), 7.98 (dd, J=5.0, 8.7 Hz, 2H), 7.42 (d, J=8.3 Hz, 1H), 7.27 (t, J=8.7 Hz, 2H), 7.12 (m, 2H), 6.80 (dd, 1H, J=4.9, 7.8 Hz, 1H), 4.79 (t, J=7.4 Hz, 1H), 4.42 (q, J=7.1 Hz, 2H), 2.87 (m, 1H), 2.73 (m, 1H), 2.27 (m, 1H), 1.82 (m, 1H), 1.42 (t, J=7.2 Hz, 3H).

Example 12

Preparation of Compound 122

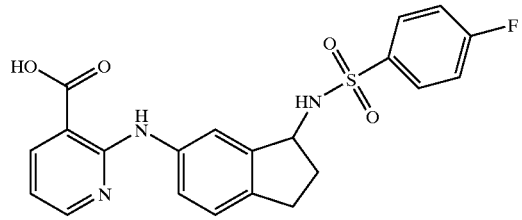

Compound 121 (75 mg, 0.165 mmol) was dissolved in 1 mL of aqueous 1N sodium hydroxide solution and 1 mL of tetrahydrofuran. This mixture was stirred for 24 hours and then acidified to pH=2 with an aqueous solution of 1N hydrochloric acid. The mixture was extracted with ethyl acetate, dried over sodium sulfate, and filtered. Evaporation of the solvent gave the crude product as a white solid (70 mg, 99%). Compound 122 was used without any further purification.

Example 13

Preparation of Compound 58

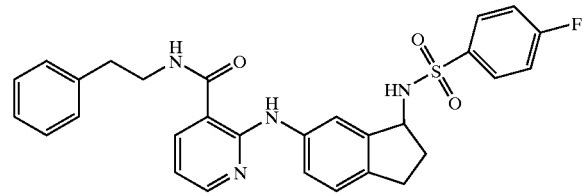

The carboxylic acid compound 122 (23 mg, 0.054 mmol), N,N'-dicyclohexylcarbodiimide (12 mg, 0.058 mmol), and N-hydroxysuccinimide (8 mg, 0.07 mmol) were combined in 1 ml of tetrahydrofuran and stirred at room temperature for five hours. The reaction mixture was filtered through a small plug of silica gel and phenethylamine (8 mg) was added to the filtrate. The reaction mixture was stirred at room temperature for 18 hours, diluted with aqueous sodium bicarbonate, and extracted with ethyl acetate. The organic layer was dried over sodium sulfate. Compound 58 was obtained as a white foam in 34% yield after flash chromatography using a 1:1:1 mixture of ethyl acetate:methylene chloride:hexanes as the eluent. $^1$H NMR (acetone-$d_6$ 300 MHz) δ (ppm): 10.91 (s, 1H), 8.27 (d, 1H, J=4.7 Hz), 8.07 (dd, 2H, J=5.2, 8.7 Hz), 7.99 (d, 2H, J=7.6 Hz), 7.65 (d, 1H, J=8.2 Hz), 7.40 (m, 3H), 7.30 (d, 4H, J=4.3 Hz), 7.21 (m, 1H), 6.75 (dd, 1H, J=4.8, 7.6 Hz), 4.84 (m, 1H), 3.68 (m, 2H), 2.97 (t, 2H, J=7.4 Hz), 2.70 (m, 1H), 2.25 (m, 1H), 1.82 (m, 1H), 1.29 (m, 1H). LC/MS (EI) found: 531.0 (M+H).

Example 14
Preparation of Compound 57

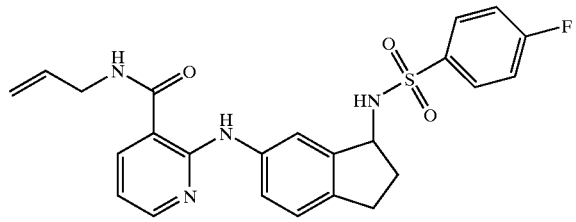

Compound 57 was produced as described for compound 58 using allylamine instead of phenethylamine in 55% yield: $^1$H NMR (acetone-$d_6$ 300 MHz) δ (ppm): 10.93 (s, 1H), 8.28 (d, 1H, J=4.7 Hz), 8.07 (m, 3H), 7.64 (d, 1H, J=8.1 Hz), 7.39 (m, 3H), 7.11 (d, 1H, J=8.2 Hz), 6.78 (dd, 1H, J=4.9, 7.6 Hz), 5.96 (m, 1H), 5.26 (d, 1H, J=17.3 Hz), 5.12 (d, 1H, J=9.2 Hz), 4.82 (m, 1H), 4.06 (m, 2H), 2.70 (m, 1H), 2.25 (m, 1H), 1.82 (m, 1H), 1.29 (m, 1H). LC/MS (EI) found: 467.1 (M+H).

Example 15
Preparation of Compound 111

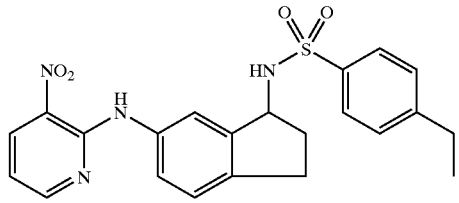

A solution of aniline compound A (633 mg, 2.0 mmol) and 2-chloro-3-nitropyridine (349 mg, 2.2 mmol) in 1-methyl-2-pyrrolidinone (4 mL) was heated at 140° C. for 23 hours, cooled to room temperature, diluted with ethyl acetate (20 mL), washed with saturated aqueous sodium bicarbonate, water, brine and dried over sodium sulfate. The crude reaction mixture was applied to a flash chromatography column. Purification by flash chromatography (2:1 hexanes-ethyl acetate) gave Compound 111 (640 mg, 73%) as an orange solid. Further purification was accomplished by recrystallization from ethyl acetate-hexanes. $^1$H NMR (300 MHz, CDCl$_3$) δ(ppm): 9.92 (1 H, s), 8.49 (1 H, dd, J=1.8, 8.3 Hz), 8.41 (1 H, dd, J=1.8, 4.5 Hz), 7.85 (2H, d, J=8.2 Hz), 7.38 (1 H, dd, J=1.8, 8.1 Hz), 7.31 (2 H, d, J=8.5 Hz), 7.26 (1 H, s), 7.16 (1 H, d, J=8.0 Hz), 6.80 (1 H, dd, J=4.5, 8.4 Hz), 4.92 (1 H, t, J=9.2 Hz), 4.83 (1 H, q, J=8.4 Hz), 2.93–83 (1 H, m), 2.77–2.67 (1 H, m), 2.70 (2 H, q, J=7.6 Hz), 2.42–2.33 (1 H, m), 1.80–1.71 (1 H, m), 1.23 (3 H, t, J=7.6 Hz); $^{13}$C NMR (75 MHz, CDCl$_3$) δ (ppm): 155.39, 150.40, 149.72, 143.13, 139.68, 138.38, 136.53, 135.60, 128.69, 127.28, 125.20, 123.42, 118.91, 113.89, 58.77, 35.10, 29.66, 28.81, 15.15.

Example 16
Preparation of Compound 112

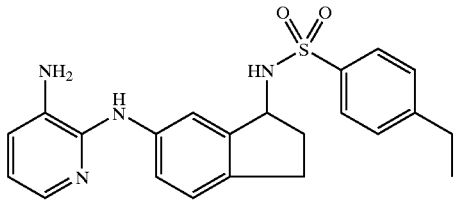

To the nitro compound (Compound 111) (363 mg, 0.83 mmol) in tetrahydrofuran (4 mL) and methanol (1.4 mL) at 0° C. was added nickel (II) chloride (11 mg, 0.08 mmol), followed by sodium borohydride (125 mg, 3.32 mmol). After the addition, the reaction mixture was stirred at room temperature for two hours, quenched with 1N sodium hydroxide (10 mL), diluted with ethyl acetate (30 mL), washed with water, brine and then dried over sodium sulfate. Compound 112 (308 mg, 91%) was used without further purification.

Example 17
Preparation of Compound 1

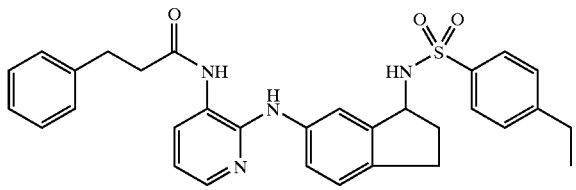

To a solution of compound 112 (50 mg, 0.12 mmol) in tetrahydrofuran (1 mL) was added triethylamine (26 µL, 0.18 mmol) followed by hydrocinnamoyl chloride (21 µL, 0.14 mmol). After 20 hours, the reaction mixture was diluted with ethyl acetate (10 mL), washed with saturated aqueous sodium bicarbonate, water, brine and then dried over sodium sulfate. Purification by flash chromatography (1:1 hexanes-ethyl acetate) gave Compound 1 which was further purified by preparative HPLC to give Compound 1 (14 mg, 21%) as a white solid. $^1$H NMR (300 MHz, CDCl$_3$) δ (ppm): 9.50 (1 H, s), 9.37 (1 H, s), 8.15 (1 H, d, J=7.7 Hz), 7.74 (2 H, d, J=8.2 Hz), 7.34 (1 H, d, J=8.2 Hz), 7.24–7.12 (5 H, m), 7.07 (1 H, d, J=8.1 Hz), 6.96 (1 H, s), 6.87 (1 H, d, J=8.0 Hz), 6.78 (1 H, d, J=7.8 Hz), 6.69 (1 H, t, J=7.1 Hz), 4.72 (1 H, bq, J=7.3 Hz), 2.97 (2 H, t, J=7.5 Hz), 2.72 (2 H, t, J=7.8 Hz), 2.65 (2 H, q, J=7.7 Hz), 2.70–2.54 (2 H, m), 2.16–2.02 (1 H, m), 1.68–1.54 (1 H, m), 1.21 (3 H, t, J=7.4 Hz). LC/MS (EI) found: 541.3 (M+H).

BioAssays

The cloning, construction and testing of CHO cells that express human voltage-gate potassium channels are described in prior U.S. patent application Ser. No. 08/893, 160 (published as WO 98/04521, see also U.S. Pat. No. 6,083,986), as are assays for measuring $^{86}$rubidium efflux from cell monolayers; fluorescence measurement of cell membrane potential; electrophysiological studies and lymphocyte proliferation studies, all of which are incorporated herein by reference.

The efficacy of various compounds of the present invention as inhibitors of Kv1.5 are shown in Table 2 (using the known patch clamp techniques cited above and described in detail in WO 98/04521 (see also U.S. Pat. No. 6,083,986), the disclosure of which is incorporated herein by reference)

TABLE 2

| Compound | % Inhibition at 0.1 μM |
|---|---|
| 1 | 46 |
| 26 | 38 |
| 27 | 43 |
| 37 | 35 |
| 42 | 45 |
| 58 | 27 |
| 59 | 20 |

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention. Those skilled in the art will recognize variations in the processes as described above and will recognize appropriate modifications based on the above disclosure for making and using the compounds of the invention.

We claim:

1. A compound having potassium channel inhibitory activity of formula (I), or a pharmaceutically acceptable salt thereof:

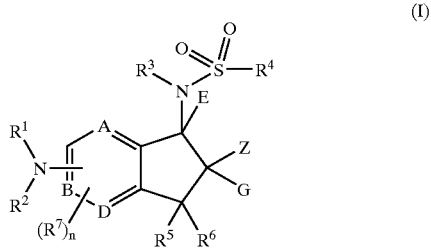

(I)

wherein,

A, B, and D are substituted carbon atoms;

E is hydrogen, or alkyl; G is hydrogen, or alkyl; or E and G taken together form a bond (site of unsaturation);

$R^1$ is selected from hydrogen, alkyl, carbocycloalkyl, aryl, (aryl)alkyl, heterocyclo, (heterocyclo)alkyl, heteroaryl, and (heteroaryl)alkyl;

$R^2$ is selected from alkyl, carbocycloalkyl, aryl, (aryl)alkyl, heterocyclo, (hetercyclo)alkyl, heteroaryl, and (heteroaryl)alkyl, each of which may be optionally substituted;

$R^3$ is selected from hydrogen (H), alkyl, carbocycloalkyl, aryl, (aryl)alkyl, heterocyclo, (heterocyclo)alkyl, heteroaryl, (heteroaryl)alkyl, aminoalkyl; substituted aminoalkyl, carboxyalkyl, alkoxyalkanoyl, aminoalkanoyl, substituted aminoalkanoyl, alkanoylamidoalkyl, alkanoyl(substituted amido)alkyl, aroylamidoalkyl, aroyl(substituted amido)alkyl, heterocyclocarbonylamidoalkyl, heterocyclocarbonyl(substituted amido)alkyl, heteroaroylamidoalkyl, and heteroaroyl(substituted amido)alkyl;

$R^4$ is selected from alkyl, carbocycloalkyl, aryl, (aryl) alkyl, heteroaryl and heterocyclo;

$R^5$ and $R^6$ are each independently selected from hydrogen, fluoro and alkyl;

$R^7$ is independently selected from hydrogen, alkyl, hydroxy, alkoxy, amino, substituted amino, nitro, cyano, halo, carboxy, alkoxycarbonyl, aminocarbonyl, substituted aminocarbonyl and n is 1, 2 or 3; and Z is selected from hydrogen, alkyl, hydroxy, SH, alkoxy, aryloxy, alkylthio, amino, substituted amino, alkoxycarbonyl, alkanoylamido, aroylamido, heterocyclocarbonylamido, heteroaroylamido, alkanoyl(alkylsubstituted) amido, aroyl(alkylsubstituted)amido, heteroaroyl(alkylsubstituted) amido, and heterocyclocarbonyl(alkyl substituted) amido.

2. The compound of claim 1 having potassium channel inhibitory activity, or a pharmaceutically acceptable salt thereof wherein $R^2$ is

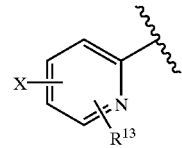

wherein

X is selected from substituted amino, —N($R^8$)CO$R^9$, —N($R^8$)SO$_2R^{10}$, and —CO—NR$^{11}$R$^{12}$;

$R^8$ is selected from hydrogen (H), alkyl, aryl and heteroaryl;

$R^9$ is selected from alkyl, carbocycloalkyl, alkenyl, alkynyl, aryl, alkoxy, aryloxy, heterocyclo, heteroaryl, (aryl)alkyl, (heteroaryl)alkyl, amino and substituted amino;

$R^{10}$ is selected from alkyl, carbocycloalkyl, aryl, heterocyclo and heteroaryl;

$R^{11}$ and $R^{12}$ are independently selected from hydrogen (H), alkyl, carbocycloalkyl, aryl, heterocyclo, heteroaryl, (aryl)alkyl, (heterocyclo)alkyl, (heteroaryl)alkyl, aminoalkyl, and substituted aminoalkyl, or $R^{11}$ and $R^{12}$ taken together with the nitrogen atom to which they are attached form a 4-membered to 8-membered heterocyclic ring;

$R^{13}$ is selected from hydrogen (H), alkyl, aryl, hydroxy, alkoxy, amino, substituted amino, nitro, cyano and halo.

3. The compound of claim 1 having potassium channel inhibitory activity, or a pharmaceutically acceptable salt thereof wherein E, G and $R^7$ are each hydrogen and n is 3.

4. The compound of claim 3 having potassium channel inhibitory activity, or a pharmaceutically acceptable salt thereof wherein, $R^5$ and $R^6$ are each hydrogen.

5. The compound of claim 2 having potassium channel inhibitory activity, or a pharmaceutically acceptable salt thereof wherein E, G, and $R^7$ are each hydrogen and n is 3.

6. The compound of claim 5 having potassium channel inhibitory activity, or a pharmaceutically acceptable salt thereof wherein, $R^5$ and $R^6$ are each hydrogen.

7. The compound of claim 1 having potassium channel inhibitory activity, said compound having the following formula (III), or a pharmaceutically acceptable salt thereof:

(III)

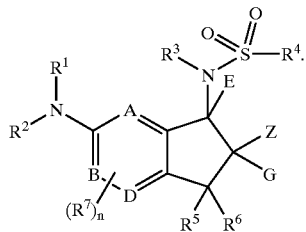

8. The compound of claim 7 having potassium channel inhibitory activity, or a pharmaceutically acceptable salt thereof wherein $R^2$ is

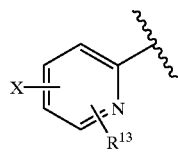

wherein

X is selected from —N($R^8$)CO$R^9$ and —CO—N$R^{11}R^{12}$;

$R^8$ is selected from H and alkyl;

$R^9$ is selected from alkyl, carbocycloalkyl, alkenyl, alkynyl, aryl, alkoxy, aryloxy, heterocyclo, heteroaryl, (aryl)alkyl, (heteroaryl)alkyl, amino and substituted amino;

$R^{11}$ and $R^{12}$ are independently selected from hydrogen (H), alkyl, carbocycloalkyl, aryl, heterocyclo, heteroaryl, (aryl)alkyl, (heterocyclo)alkyl, (heteroaryl)alkyl, aminoalkyl, and substituted aminoalkyl, or $R^{11}$ and $R^{12}$ taken together with the nitrogen atom to which they are attached form a 4-membered to 8-membered heterocyclic ring; and $R^{13}$ is selected from hydrogen, alkyl, hydroxy, alkoxy, amino, substituted amino, nitro, cyano and halo.

9. The compound of claim 7 having potassium channel inhibitory activity, or a pharmaceutically acceptable salt thereof wherein E, G and $R^7$ are each hydrogen and n is 3.

10. The compound of claim 9 having potassium channel inhibitory activity, or a pharmaceutically acceptable salt thereof wherein, $R^5$ and $R^6$ are each hydrogen.

11. The compound of claim 8 having potassium channel inhibitory activity, or a pharmaceutically acceptable salt thereof wherein E, G and $R^7$ are each hydrogen and n is 3.

12. The compound of claim 11 having potassium channel inhibitory activity, or a pharmaceutically acceptable salt thereof wherein, $R^5$ and $R^6$ are each hydrogen.

13. The compound of claim 1, 3, 4, 7, 9 or 10 having potassium channel inhibitory activity, or a pharmaceutically acceptable salt thereof, wherein $R^3$ is selected from hydrogen and alkyl;

$R^4$ is selected from aryl and heteroaryl and

Z is selected from hydrogen, hydroxyl, amino and substituted amino.

14. The compound of claim 2, 5, 6, 8, 11, or 12 having potassium channel inhibitory activity, or a pharmaceutically acceptable salt thereof, wherein $R^3$ is selected from hydrogen and alkyl;

$R^4$ is selected from aryl and heteroaryl and

Z is selected from hydrogen, hydroxyl, amino and substituted amino.

15. A pharmaceutical composition comprising the compound of claim 1, 2, 3, 4, 5, 6, 7, 8, 9, 10, 11, or 12, or a pharmaceutically acceptable salt thereof and a pharmaceutically acceptable diluent or carrier.

16. A pharmaceutical composition comprising the compound of claim 13, or a pharmaceutically acceptable salt thereof and a pharmaceutically acceptable diluent or carrier.

17. A pharmaceutical composition comprising the compound of claim 14, or a pharmaceutically acceptable salt thereof and a pharmaceutically acceptable diluent or carrier.

18. A method for inhibiting potassium transport across cellular membranes possessing potassium channels comprising exposing a cell membrane possessing said channels to the presence of a compound of claim 1, 2, 3, 4, 5, 6, 7, 8, 9, 10, 11, or 12, or a pharmaceutically acceptable salt thereof.

19. The method of claim 18 wherein the potassium channel is a voltage gated potassium channel.

20. The method of claim 19 wherein the potassium channel is selected from a potassium channel responsible for cardiac $I_{Kur}$ potassium current, a potassium channel responsible for T-lymphocyte $I_{Kn}$ potassium current and potassium channels containing one of Kv1.5 or Kv1.3 α-subunit gene products.

21. A method for treating cardiac arrhythmias which comprises administering to a patient in need thereof, a pharmaceutically effective amount of a compound of claim 1, 2, 3, 4, 5, 6, or 7, or a pharmaceutically acceptable salt thereof.

* * * * *

UNITED STATES PATENT AND TRADEMARK OFFICE
CERTIFICATE OF CORRECTION

PATENT NO. : 6,849,634 B2
DATED : February 1, 2005
INVENTOR(S) : Serge Beaudoin et al.

It is certified that error appears in the above-identified patent and that said Letters Patent is hereby corrected as shown below:

Title page,
Item [56], References Cited, OTHER PUBLICATIONS, delete:
"International Search Report dated Jul. 7, 2002.
Gisbert Schneider, et al. "*Virtual Screening For Bioactive Molecules by Evolutionary De Novo Desing*", Angewandte Chemie, International Edition (200), 39(22), 4130-4133" insert:
-- Doupnik, et al., "*The Inward Rectifier Potassium Channel Family,*" Current Opinion in Neurobiology, 1995, 5:268-277.
Chandy, et al., "*Voltage-Gated Potassium Channel Genes,*" Handbook of Receptors and Channels, 1-71 (1995).
Epps et al., "*Chemistry and Physics of Lipids, 69 (1994) pp. 137-150.*
WO 95-18617 Abstract
Chem. Abs., Vol. 104, No. 9 Abs, No. 68632 (03/03/86).
International Search Report PCT/US97/12559.
Dialog Web Output, Derwent World Patents Index, Records for: pn=EP 915087.
International Search Report PCT/US 00/34765. --.

Signed and Sealed this

Twentieth Day of December, 2005

JON W. DUDAS
*Director of the United States Patent and Trademark Office*